US007571055B2

(12) United States Patent
Behrens et al.

(10) Patent No.: US 7,571,055 B2
(45) Date of Patent: Aug. 4, 2009

(54) SYSTEMIC LUPUS ERYTHEMATOSUS

(75) Inventors: Timothy W. Behrens, Minnetonka, MN (US); Emily C. Gillespie, Savage, MN (US); Peter K. Gregersen, Larchmont, NY (US)

(73) Assignees: Regents of the University of Minnesota, Sint Paul, MN (US); The Feinstein Institute for Medical Research, Manhasset, NY (US)

( * ) Notice: Subject to any disclaimer, the term of this patent is extended or adjusted under 35 U.S.C. 154(b) by 1 day.

(21) Appl. No.: 11/251,589

(22) Filed: Oct. 13, 2005

(65) Prior Publication Data

US 2006/0177814 A1    Aug. 10, 2006

Related U.S. Application Data

(60) Provisional application No. 60/618,442, filed on Oct. 13, 2004.

(51) Int. Cl.
*G06F 19/00* (2006.01)
*C12Q 1/68* (2006.01)

(52) U.S. Cl. ............................................. 702/19; 435/6
(58) Field of Classification Search ....................... None
See application file for complete search history.

(56) References Cited

U.S. PATENT DOCUMENTS

| 5,143,854 | A | 9/1992 | Pirrung et al. |
| 5,744,305 | A | 4/1998 | Fodor et al. |
| 6,905,827 | B2 | 6/2005 | Wohlgemuth et al. |
| 7,118,865 | B2 | 10/2006 | Behrens et al. |
| 2003/0148298 | A1 | 8/2003 | O'Toole et al. |
| 2004/0009479 | A1 | 1/2004 | Wohlgemuth et al. |

FOREIGN PATENT DOCUMENTS

| WO | WO 00/22093 | 4/2000 |
| WO | WO 03/090694 | 11/2000 |
| WO | WO 02/057414 | 7/2002 |

OTHER PUBLICATIONS

Alarcón et al., "Systemic Lupus Erythematosus in Three Ethnic Groups," *Arthritis Rheum.*, 1998, 41(7):1173-1180.
Arnett and Reveille, "Genetics of Systemic Lupus Erythematosus," *Rheum. Dis. Clin. N. Am.*, 1992, 18(4):865-892.
Asmal et al., "Production of Ribosome Components in Effector CD4+T Cells is Accelerated by TCR Stimulation and Coordinated by ERK-MAPK," *Immunity*, 2003, 19:535-548.
Bae et al., "Reliability and validity of systemic lupus activity measure-revised (SLAM-R) for measuring clinical disease activity in systemic lupus erythematosus," *Lupus*, 2001, 10:405-409.
Baechler et al., "Interferon-inducible gene expression signature in peripheral blood cells of patients with severe lupus," *Proc. Natl. Acad. Sci. USA*, 2003, 100(5):2610-2615.
Baechler et al., "Expression levels for many genes in human peripheral blood cells are highly sensitive to ex vivo incubation," *Genes and Immunity*, 2004, 5:347-353.
Balomenos et al., "Interferon-γ is Required for Lupus-like Disease and Lymphoaccumulation in MRL-*lpr* Mice," *J. Clin. Invest.*, 1998, 101(2):364-371.
Bennett et al., "Interferon and Granulopoiesis Signatures in Systemic Lupus Erythematosus Blood," *J. Exp. Med.*, 2003, 197(6):711-723.
Blanco et al., "Induction of Dendritic Cell Differentiation by IFN-α in Systemic Lupus Erythematosus," *Science*, 2001, 294:1540-1543.
Bombardier et al., "Derivation of the SLEDAI. A Disease Activity Index for Lupus Patients," *Arthritis Rheum.*, 1992, 35(6):630-640.
Braun et al., "Type I Interferon controls the onset and severity of autoimmune manifestations in *lpr* mice," *J. Autoimmun.*, 2003, 20:15-25.
Buttrum et al., "Changes in neutrophil rheology after acute ischemia and reperfusion in the rat hindlimb," *J. Lab. Clin. Med.*, 1996, 128(5):506-514.
Coleman, "Of mouse and man—what is the value of the mouse in predicting gene expression in humans?" *Drug Discovery Today*, 2003, 8(6):233-235.
de Veer et al., "Functional classification of interferon-stimulated genes identified using microarrays," *J. Leukocyte Biology*, 2001, 69:912-920.
Der et al., "Identification of genes differentially regulated by interferon α, β, or γ using oligonucleotide arrays," *Proc. Natl. Acad. Sci. USA*, 1998, 95:15623-15628.
Dörner and Lipsky, "Correlation of circulating $CD27^{high}$ plasma cells and disease activity in systemic lupus erythematosus" *Lupus*, 2004, 13:283-289.
Eisen et al., "Cluster analysis and display of genome-wide expression patterns," *Proc. Natl. Acad. Sci. USA*, 1998, 95:14863-14868.
Fukuyama et al., "Systemic Lupus Erythematosus After β-Interferon Therapy for Chronic Hepatitis C: A Case Report and Review of the Literature," *Am. J. Gastroenterol.*, 2000, 95(1):310-312.
Gergely, Jr. et al., "Persistent Mitochondrial Hyperpolarization, Increased Reactive Oxygen Intermediate Production, and Cytoplasmic Alkalinization Characterize Altered IL-10 Signaling in Patients with Systemic Lupus Erythematosus," *J. Immunol.*, 2002, 169:1092-1101.

(Continued)

*Primary Examiner*—John S Brusca
(74) *Attorney, Agent, or Firm*—Fish & Richardson P.C.

(57) ABSTRACT

This document relates to methods and materials involved in diagnosing SLE. For example, this document relates to methods and materials involved in diagnosing SLE, diagnosing severe SLE, and assessing a mammal's susceptibility to develop severe SLE. For example, this document provides nucleic acid arrays that can be used to diagnose SLE in a mammal. Such arrays can allow clinicians to diagnose SLE based on a simultaneous determination of the expression levels of many genes that are differentially expressed in SLE patients as compared to healthy controls. In addition, methods and materials for assessing SLE activity, determining the likelihood of experiencing active SLE, and detecting SLE treatment effectiveness are provided herein.

14 Claims, 9 Drawing Sheets

OTHER PUBLICATIONS

Gibson, "Simulated evolution and artificial selection," *BioSystems*, 1989, 23:219-229.

Ginsburg et al., "Circulating and pokeweed mitogen-induced immunoglobulin-secreting cells in systemic lupus erythematosus," *Clin. Exp. Immunol.*, 1979, 35:76-88.

Gladman et al., "The development and initial validation of the Systemic Lupus International Collaborating Clinics/American College of Rheumatology damage index for systemic lupus erythematosus," *Arthritis Rheum.*, 1996, 39(3):363-369.

Gregersen and Brehrens, "Fine mapping the phenotype in autoimmune disease: the promise and pitfalls of DNA microarray technologies," *Genes and Immunity*, 2003, 4:175-176.

Gu et al., "Analysis of inflammation related gene expression spectrum in ankylosing spondylitis patients using cDNA microarray," *Zhonghua Yi Xue Za Zhi*, 2001, 81(17):1030-1034 (Abstract only—article is in Chinese).

Harada et al., "Identification of early plasma cells in peripheral blood and their clinical significance," *Br. J. Haematol.*, 1996, 92:184-191.

Hay et al., "The BILAG index: a reliable and valid instrument for measuring clinical disease activity in systemic lupus erythematosus," *Q. J. Med.*, 1993, 86:447-458.

Hirano et al., "Roles of STAT3 in mediating the cell growth, differentiation and survival signals relayed through the IL-6 family of cytokine receptors," *Oncogene*, 2000, 19:2548-2556.

Hochberg, "Updating the American College of Rheumatology Revised Criteria for the Classification of Systemic Lupus Erythematosus," *Arthritis & Rheumatism*, 1997, 40(9):1725.

Jacob et al., "In Vivo Treatment of (NZB x NZW)$F_1$ Lupus-Like Nephritis with Monoclonal Antibody to γ Interferon," *J. Exp. Med.*, 1987, 166:798-803.

Lau et al., "Further evidence of increased polymorphonuclear cell activity in patients with Raynaud's phenomenon," *Br. J. Rheumatol.*, 1992, 31:375-380.

Liang et al., "Reliability and validity of six systems for the clinical assessment of disease activity in systemic lupus erythematosus," *Arthritis Rheum.*, 1989, 32(9):1107-1118.

Liossis et al., "Immune cell biochemical abnormalities in systemic lupus erythematosus," *Clin. Exp. Rheumatol.*, 1997, 15:677-684.

Liu et al., "Comparison of differentially expressed genes in T lymphocytes between autoimmune disease and murine models of autoimmune disease," *Clinical Immunology*, 2004, 112:225-230.

Lövgren et al., "Induction of Interferon-α Production in Plasmacytoid Dendritic Cells by Immune Complexes Containing Nucleic Acid Released by Necrotic or Late Apoptotic Cells and Lupus IgG," *Arthritis Rheum.*, 2004, 50(6):1861-1872.

Pascual et al., "The central role of dendritic cells and interferon-α in SLE," *Curr. Opin. Rheumatol.*, 2003, 15:548-556.

Perl et al., "Mitochondrial hyperpolarization: a checkpoint of T-cell life, death and autoimmunity," *Trends Immunol.*, 2004, 25(7):360-367.

Petri et al., "Definition, incidence, and clinical description of flare in systemic lupus erythematosus. A prospective cohort study," *Arthritis Rheum.*, 1991, 34(8):937-944.

Rainen et al., "Stabilization of mRNA Expression in Whole Blood Samples," *Clin. Chem.*, 2002, 48(11):1883-1890.

Rascu et al., "Clinical Relevance of Fcγ Receptor Polymorphisms," *Ann. N.Y. Acad. Sci.*, 1997, 815:282-295.

Reimold et al., "Plasma cell differentiation requires the transcription factor XBP-1," *Nature*, 2001, 412:300-307.

Richards et al., "Interferon-γ is required for lupus nephritis in mice treated with the hydrocarbon oil pristane," *Kidney Int.*, 2001, 60:2173-2180.

Rönnblom and Alm, "A Pivotal Role for the Natural Interferon α-producing Cells (Plasmacytoid Dendritic Cells) in the Pathogenesis of Lupus," *J. Exp. Med.*, 2001, 194(12):F59-F63.

Rönnblom et al., "Autoimmune phenomena in patients with malignant carcinoid tumors during interferon-α treatment," *Acta Oncol.*, 1991, 30(4):537-540.

Rozzo et al., "Evidence for an Interferon-Inducible Gene, *Ifi202*, in the Susceptibility to Systemic Lupus," *Immunity*, 2001, 15:435-443.

Santiago-Raber et al., "Type-I Interferon Receptor Deficiency Reduces Lupus-like Disease in NZB Mice," *J. Exp. Med.*, 2003, 197(6):777-788.

Saraste, "Oxidative Phosphorylation at the *fin de siècle*," *Science*, 1999, 283:1488-1493.

Schur, "Genetics of systemic lupus erythematosus," *Lupus*, 1995, 4:425-437.

Seery et al., "Antinuclear Autoantibodies and Lupus Nephritis in Transgenic Mice Expressing Interferon γ in the Epidermis," *J. Exp. Med.*, 1997, 186(9):1451-1459.

Shaffer et al., "Blimp-1 Orchestrates Plasma Cell Differentiation by Extinguishing the Mature B Cell Gene Expression Program," *Immunity*, 2002, 17:51-62.

Shaffer et al., "XBP1, Downstream of Blimp-1, Expands the Secretory Apparatus and Other Organelles, and Increases Protein Synthesis in Plasma Cell Differentiation," *Immunity*, 2004, 21:81-93.

Shoenfeld et al., "Effect of Physical Effort on the White Blood Cells in Benign Familial Leukopenia," *Acta Haematol.*, 1981, 65:108-113.

Tan and Arnett, "Genetic factors in the etiology of systemic sclerosis and Raynaud phenomenon," *Curr. Opin. Rheumatol.*, 2000, 12:511-519.

Tan et al., "The 1982 Revised Criteria for the Classification of Systemic Lupus Erythematosus," *Arthritis and Rheumatism*, 1982, 25(11):1271-1277.

Vallin et al., "Patients with systemic lupus erythematosus (SLE) have a circulating inducer of interferon-alpha (IFN-α) production acting on leucocytes resembling immature dendritic cells," *Clin. Exp. Immunol.*, 1999, 115:196-202.

Vyse and Kotzin, "Genetic basis of systemic lupus erythematosus," *Curr. Opin. Immunol.*, 1996, 8:843-851.

Wakeland et al., "Delineating the Genetic Basic of Systemic Lupus Erythematosus," *Immunity*, 2001, 15:397-408.

Zhu et al., "Suppression of Autoimmune Neuritis in IFN-γ Receptor-Deficient Mice," *Exp. Neurol.*, 2001, 169:472-478.

Slide Presentation presented at SLE: Targets for New Therapeutics—A Scientific Conference, Salmon et al. (organizers), Jan. 10-12, 2002, Hyatt Regency Bethesda, Bethesda, Maryland.

Saetre et al., "From wild wolf to domestic dog: gene expression changes in the brain," *Molec. Brain Res.*, 2004, 126:198-206.

Figure 6A

|        | Group 0 | Group 1 | Group 2 | Group 3 |
|--------|---------|---------|---------|---------|
| IFN:   | +       | −       | +       | +       |
| R/M:   | +       | +       | −       | +       |
| N/T:   | +       | −       | −       | −       |

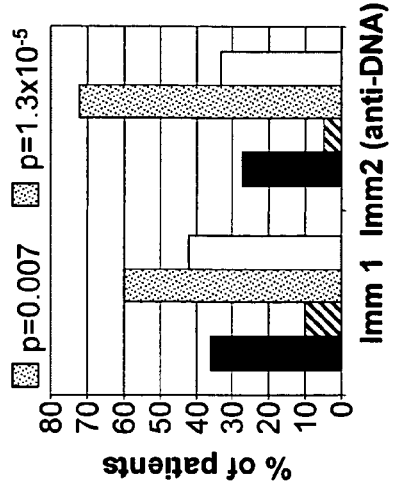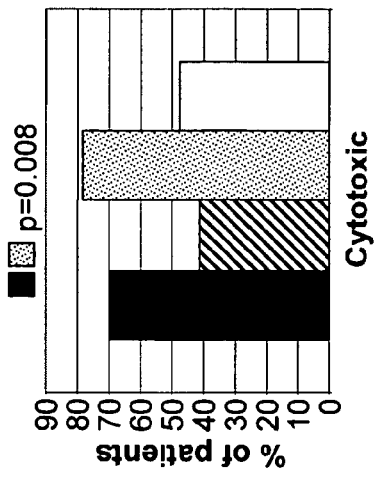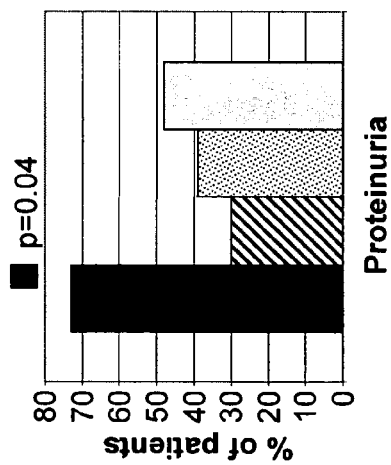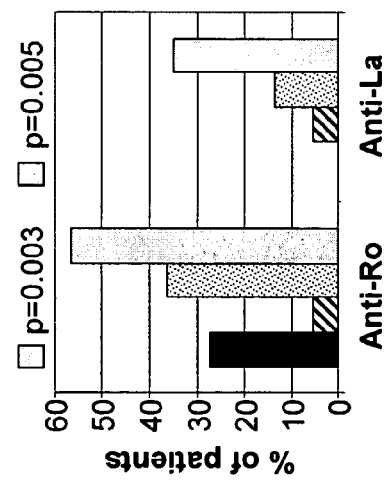

SYSTEMIC LUPUS ERYTHEMATOSUS

CROSS-REFERENCE TO RELATED APPLICATION

This application claims the benefit of U.S. Provisional Application Ser. No. 60/618,442, filed Oct. 13, 2004, which is incorporated by reference in its entirety into this specification.

STATEMENT AS TO FEDERALLY SPONSORED RESEARCH

Funding for the work described herein was provided in part by the National Institute of Arthritis and Musculoskeletal Diseases (grant no. NIH N01-AR12256). The federal government thus may have certain rights in the invention.

BACKGROUND

1. Technical Field

This document relates to methods and materials involved in diagnosing systemic lupus erythematosus (SLE). For example, this document relates to methods and materials involved in diagnosing SLE, diagnosing severe SLE, assessing a mammal's susceptibility to develop severe SLE, and assessing SLE activity.

2. Background Information

SLE is a chronic, inflammatory autoimmune disease characterized by the production of autoantibodies having specificity for a wide range of self-antigens. SLE autoantibodies mediate organ damage by directly binding to host tissues and by forming immune complexes that deposit in vascular tissues and activate immune cells. Organs targeted in SLE include the skin, kidneys, vasculature, joints, various blood elements, and the central nervous system (CNS). The severity of disease, the spectrum of clinical involvement, and the response to therapy vary widely among patients. This clinical heterogeneity makes it challenging to diagnose and manage lupus.

SUMMARY

This document relates to methods and materials involved in diagnosing SLE. For example, this document relates to methods and materials involved in diagnosing SLE, diagnosing severe SLE, assessing a mammal's susceptibility to develop severe SLE, and assessing SLE activity. For example, this document provides nucleic acid arrays that can be used to diagnose SLE in a mammal. Such arrays can allow clinicians to diagnose SLE based on a determination of the expression levels of many genes that are differentially expressed in SLE patients as compared to healthy controls. This document also provides methods and materials that can be used to assess SLE activity. Assessing SLE activity can allow clinicians to identify patients with active SLE. In addition, this document provides methods and materials that can be used to assess the likelihood that a patient will experience active SLE. For example, a patient found to have cells expressing one or more genes listed in Table 19 at a level that is greater than or less than the average level observed in control cells can be classified as being likely to experience active SLE. This document also provides methods and materials that can be used to determine whether or not a mammal responds to an SLE treatment. For example, patients receiving an SLE treatment (e.g., an anti-IFN treatment) who are found to no longer express one or more genes within an IFN signature at a level greater than or less than the average level observed in control cells can be classified as responding to that SLE treatment.

In addition, this document provides methods and materials involved in diagnosing SLE conditions that are accompanied by activation of an interferon pathway. For the purpose of this document, the term "SLE accompanied by activation of an interferon pathway" (abbreviated "SLE-AIP") refers to any SLE condition that coexists with or is caused by activation of an interferon pathway. Activation of an interferon pathway refers to a state where interferon-regulated genes that are up-regulated in response to interferon are up-regulated, and where interferon-regulated genes that are down-regulated in response to interferon are down-regulated. Typically, activation of an interferon pathway results in the presence of a gene expression profile that is similar to the gene expression profile observed in cells that were treated with interferon. An interferon pathway can be activated regardless of the presence or absence of detectable levels of interferon. For example, an SLE patient can have low levels of detectable interferon while exhibiting a gene expression profile characteristic of an activated interferon pathway. Such an SLE patient can be diagnosed as having SLE-AIP.

Diagnosing patients as having SLE-AIP can help clinicians determine appropriate treatments for those patients. For example, a clinician who diagnoses a patient as having SLE-AIP can treat that patient with medication that improves both the patient's SLE symptoms and aberrant activation of an interferon pathway. In some cases, a single medication can be used to reverse a patient's activation of an interferon pathway such that the patient's SLE symptoms are reduced or relieved. Thus, treating a patient having SLE-AIP by modulating the level of interferon pathway activation can improve that patient's health and quality of life by, for example, reducing the symptoms associated with SLE.

Typically, a diagnosis of SLE can be made on the basis of 11 criteria defined by the American College of Rheumatology (ACR). These criteria include malar rash, discoid rash, photosensitivity, oral ulcers, arthritis, serositis, renal disorder, neurologic disorder, hematologic disorder, immunologic disorder, and antinuclear antibody (Tan et al. (1982) *Arthritis Rheum.* 25:1271-1277). A mammal (e.g., a human) can be clinically diagnosed with SLE if he or she meets at least four of the eleven criteria. The term "severe SLE" as used herein refers to an SLE condition where the patient has one or more of the following: renal, central nervous system, or hematologic involvement.

This document is based, in part, on the discovery of genes that are differentially expressed between SLE patients and healthy controls. This document also is based, in part, on the discovery that the expression levels of these genes can be used to distinguish mammals with SLE from healthy mammals. For example, the expression levels for the genes listed in Table 1 can be assessed to diagnose SLE. In addition, this document is based, in part, on the discovery that a portion of SLE patients can have SLE associated with or caused by activation of an interferon pathway. For example, SLE patients having severe SLE can be, at least partially, dependent upon the presence of an activated interferon pathway. Further, this document is based, in part, on the discovery of genes that are differentially expressed between SLE-AIP patients and SLE patients not associated with an activated interferon pathway. For example, the expression levels for the genes listed in Table 4 can be assessed to diagnose SLE-AIP.

For the purpose of this document, the term "IFN signature 1" as used herein refers to an expression profile where one or more (e.g., two, three, four, five, six, seven, eight nine, ten, 15, 20, 25, 30, 35, 40, 45, 50, 55, 60, 65, or more) of the genes listed in Table 5 are overexpressed as compared to control cells from a control mammal (e.g., PBMCs from a healthy human). In some cases, the IFN signature 1 can be an expression profile where 10, 20, 30, 40, 50, 60, 70, 80, 90, or 100 percent of the genes listed in Table 5 are overexpressed as compared to control cells from a control mammal. The term "activity signature 1" as used herein refers to an expression profile where one or more (e.g., two, three, four, five, six, seven, eight nine, ten, 15, 20, 25, 30, 35, 40, 45, 50, 55, 60, 65, or more) of the genes listed in Table 16 are differentially expressed as compared to control cells from a control mammal (e.g., PBMCs from a healthy human). In some cases, the activity signature 1 can be an expression profile where 10, 20, 30, 40, 50, 60, 70, 80, 90, or 100 percent of the genes listed in Table 16 are differentially expressed as compared to control cells from a control mammal. The term "activity signature 2" as used herein refers to an expression profile where one or more (e.g., two, three, four, five, six, seven, eight nine, ten, 15, 20, 25, 30, 35, 40, 45, 50, 55, 60, 65, or more) of the genes listed in Table 17 are differentially expressed as compared to control cells from a control mammal (e.g., PBMCs from a healthy human). In some cases, the activity signature 2 can be an expression profile where 10, 20, 30, 40, 50, 60, 70, 80, 90, or 100 percent of the genes listed in Table 17 are differentially expressed as compared to control cells from a control mammal. The term "activity signature 3" as used herein refers to an expression profile where one or more (e.g., two, three, four, five, six, seven, eight nine, ten, 15, 20, 25, 30, 35, 40, 45, 50, 55, 60, 65, or more) of the genes listed in Table 19 are differentially expressed as compared to control cells from a control mammal (e.g., PBMCs from a healthy human). In some cases, the activity signature 3 can be an expression profile where 10, 20, 30, 40, 50, 60, 70, 80, 90, or 100 percent of the genes listed in Table 19 are differentially expressed as compared to control cells from a control mammal.

In one aspect, this document features a method for diagnosing severe systemic lupus erythematosus. The method can include (a) determining whether or not a mammal contains cells that express at least 2 of the genes listed in Table 5 to an extent greater than or less than the average level of expression exhibited in control cells from one or more control mammals, wherein the mammal and the one or more control mammals are from the same species; and (b) diagnosing the mammal as having severe systemic lupus erythematosus if the mammal contains the cells and diagnosing the mammal as not having severe systemic lupus erythematosus if the mammal does not contain the cells. The mammal can be a human. The one or more control mammals can be healthy humans. The one or more control mammals can be humans with mild systemic lupus erythematosus. The cells and the control cells can be peripheral blood mononuclear cells. The method can include determining whether or not the mammal contains cells that express at least 5 of the genes or at least 10 of the genes to an extent greater than or less than the level of expression exhibited in the control cells. The extent can be greater than or less than the average level of expression exhibited in control cells from at least 10 control mammals or from at least 20 control mammals. The determining step can include measuring the level of mRNA expressed from at least 2 of the genes or from at least 5 of the genes.

In another aspect, this document features a method for assessing the predisposition of a mammal to develop severe systemic lupus erythematosus. The method can include (a) determining whether or not the mammal contains cells that express at least 2 of the genes listed in Table 5 to an extent greater than or less than the average level of expression exhibited in control cells from one or more control mammals, wherein the mammal and the one or more control mammals are from the same species, and (b) classifying the mammal as being susceptible to develop severe systemic lupus erythematosus if the mammal contains the cells and classifying the mammal as not being susceptible to develop severe systemic lupus erythematosus if the mammal does not contain the cells. The mammal can be a human. The one or more control mammals can be healthy humans. The one or more control mammals can be humans with mild systemic lupus erythematosus. The cells and the control cells can be peripheral blood mononuclear cells. The method can include determining whether or not the mammal contains cells that express at least 5 of the genes or at least 10 of the genes to an extent greater than or less than the level of expression exhibited in the control cells. The extent can be greater than or less than the average level of expression exhibited in control cells from at least 10 control mammals or from at least 20 control mammals. The determining step can include measuring the level of mRNA expressed from at least 2 of the genes or from at least 5 of the genes.

In another aspect, this document features a method for diagnosing systemic lupus erythematosus in a mammal. The method can include (a) determining whether or not the mammal contains cells that express at least 10 of the genes listed in Tables 5, 7, 8, 9, 16, 17, and 19 to an extent greater than or less than the average level of expression exhibited in control cells from one or more control mammals, wherein the mammal and the one or more control mammals are from the same species, and (b) diagnosing the mammal as having systemic lupus erythematosus if the mammal contains the cells and diagnosing the mammal as not having systemic lupus erythematosus if the mammal does not contain the cells.

In another aspect, the method for diagnosing systemic lupus erythematosus in a mammal can include (a) determining whether or not the mammal contains cells that express at least 5 of the genes listed in Table 7 to an extent greater than the average level of expression exhibited in control cells from one or more control mammals, wherein the mammal and the one or more control mammals are from the same species, and (b) diagnosing the mammal as having systemic lupus erythematosus if the mammal contains the cells and diagnosing the mammal as not having systemic lupus erythematosus if the mammal does not contain the cells.

In still another aspect, the method for diagnosing systemic lupus erythematosus in a mammal can include (a) determining whether or not the mammal contains cells that express at least 5 of the genes listed in Table 8 to an extent less than the average level of expression exhibited in control cells from one or more control mammals, wherein the mammal and the one or more control mammals are from the same species, and (b) diagnosing the mammal as having systemic lupus erythematosus if the mammal contains the cells and diagnosing the mammal as not having systemic lupus erythematosus if the mammal does not contain the cells.

In yet another aspect, this document features a nucleic acid array containing at least 5 nucleic acid molecules, wherein each of the at least 5 nucleic acid molecules has a different nucleic acid sequence, and wherein at least 50 percent of the nucleic acid molecules of the array include a sequence from a gene selected from the group consisting of the genes listed in Tables 5, 7, 8, 9, 16, 17, and 19. The array can contain at least 10 nucleic acid molecules, wherein each of the at least 10 nucleic acid molecules has a different nucleic acid sequence. The array can contain at least 20 nucleic acid molecules, wherein each of the at least 20 nucleic acid molecules has a different nucleic acid sequence. The array can contain at least 50 nucleic acid molecules, wherein each of the at least 50 nucleic acid molecules has a different nucleic acid sequence.

Each of the nucleic acid molecules that contain a sequence from a gene selected from the group can include no more than three mismatches. At least 75 percent (e.g., at least 95 percent) of the nucleic acid molecules of the array can contain a sequence from a gene selected from the group. The array can contain glass.

In yet another aspect, this document features a method for identifying a mammal having severe systemic lupus erythematosus. The method comprises, or consist essentially of, (a) determining whether or not a mammal contains cells having an IFN signature 1, and (b) classifying said mammal as having severe systemic lupus erythematosus if the mammal contains the cells and classifying the mammal as not having severe systemic lupus erythematosus if the mammal does not contain the cells. The mammal can be a human. The cells can be peripheral blood mononuclear cells. The IFN signature 1 can comprise, or consist essentially of, at least 10, 20, 30, 40, 50, 60, 70, 80, 90, 95, or 100 percent of the genes listed in Table 5.

In yet another aspect, this a method for assessing systemic lupus erythematosus disease activity. The method comprises, or consist essentially of, (a) determining whether or not a mammal contains cells having an activity signature 1, an activity signature 2, or an activity signature 3, and (b) classifying the mammal as having active systemic lupus erythematosus disease if the mammal contains the cells and classifying the mammal as not having active systemic lupus erythematosus disease if the mammal does not contain the cells. The mammal can be a human. The cells can be peripheral blood mononuclear cells. The method can comprise determining whether or not the mammal contains cells having the activity signature 1. The method can comprise determining whether or not the mammal contains cells having the activity signature 2. The method can comprise determining whether or not the mammal contains cells having the activity signature 3. The activity signature 1 can comprise, or consist essentially of, at least 10, 20, 30, 40, 50, 60, 70, 80, 90, 95, or 100 percent of the genes listed in Table 16. The activity signature 2 can comprise, or consist essentially of, at least 10, 20, 30, 40, 50, 60, 70, 80, 90, 95, or 100 percent of the genes listed in Table 17. The activity signature 3 can comprise, or consist essentially of, at least 10, 20, 30, 40, 50, 60, 70, 80, 90, 95, or 100 percent of the genes listed in Table 19.

In yet another aspect, this document features a method for assessing systemic lupus erythematosus disease activity. The method comprises, or consists essentially of, (a) determining whether or not a mammal contains cells that express at least 2 of the genes listed in Table 16, 17, or 19 to an extent greater than or less than the average level of expression exhibited in control cells from one or more control mammals, wherein the mammal and the one or more control mammals are from the same species; and (b) classifying the mammal as having active systemic lupus erythematosus disease if the mammal contains the cells and classifying the mammal as not having active systemic lupus erythematosus disease if the mammal does not contain the cells. The mammal can be a human. The one or more control mammals can be healthy humans. The one or more control mammals can be humans with inactive systemic lupus erythematosus. The cells and the control cells can be peripheral blood mononuclear cells. The method can include determining whether or not the mammal contains cells that express at least 5 of the genes or at least 10 of the genes to an extent greater than or less than the level of expression exhibited in the control cells. The extent can be greater than or less than the average level of expression exhibited in control cells from at least 10 control mammals or from at least 20 control mammals. The determining step can include measuring the level of mRNA expressed from at least 2 of the genes or from at least 5 of the genes.

In yet another aspect, this document features a method for identifying a mammal likely to experience active systemic lupus erythematosus disease. The method comprises, or consists essentially of, (a) determining whether or not a mammal having systemic lupus erythematosus disease contains cells having an activity signature 3, and (b) classifying the mammal as being likely to experience the active systemic lupus erythematosus disease if the mammal contains the cells and classifying the mammal as not being likely to experience the active systemic lupus erythematosus disease if the mammal does not contain the cells. The mammal can be a human. The cells can be peripheral blood mononuclear cells. The activity signature 3 can comprise, or consist essentially of, at least 10, 20, 30, 40, 50, 60, 70, 80, 90, 95, or 100 percent of the genes listed in Table 19.

In yet another aspect, this document features a method for identifying a mammal likely to experience active systemic lupus erythematosus disease. The method comprises, or consists essentially of, (a) determining whether or not a mammal contains cells that express at least 2 of the genes listed in Table 19 to an extent greater than or less than the average level of expression exhibited in control cells from one or more control mammals, wherein the mammal and the one or more control mammals are from the same species; and (b) classifying the mammal as being likely to experience the active systemic lupus erythematosus disease if the mammal contains the cells and classifying the mammal as not being likely to experience the active systemic lupus erythematosus disease if the mammal does not contain the cells. The mammal can be a human. The one or more control mammals can be healthy humans. The one or more control mammals can be humans with inactive systemic lupus erythematosus. The cells and the control cells can be peripheral blood mononuclear cells. The method can include determining whether or not the mammal contains cells that express at least 5 of the genes or at least 10 of the genes to an extent greater than or less than the level of expression exhibited in the control cells. The extent can be greater than or less than the average level of expression exhibited in control cells from at least 10 control mammals or from at least 20 control mammals. The determining step can include measuring the level of mRNA expressed from at least 2 of the genes or from at least 5 of the genes.

In yet another aspect, this document features a method for identifying a mammal likely to respond to an anti-IFN treatment for systemic lupus erythematosus. The method comprises, or consists essentially of, (a) determining whether or not a mammal having systemic lupus erythematosus disease contains cells having an IFN signature 1, and (b) classifying the mammal as being likely to respond to the anti-IFN treatment if the mammal contains the cells and classifying the mammal as not being likely to respond to the anti-IFN treatment if the mammal does not contain the cells. The mammal can be a human. The cells can be peripheral blood mononuclear cells. The IFN signature 1 can comprise, or consist essentially of, at least 10, 20, 30, 40, 50, 60, 70, 80, 90, 95, or 100 percent of the genes listed in Table 5.

In yet another aspect, this document features a method for identifying a mammal likely to respond to an anti-IFN treatment for systemic lupus erythematosus. The method comprises, or consists essentially of, (a) determining whether or not a mammal contains cells that express at least 2 of the genes listed in Table 5 to an extent greater than or less than the average level of expression exhibited in control cells from one or more control mammals, wherein the mammal and the one or more control mammals are from the same species; and (b) classifying the mammal as being likely to respond to an anti-IFN treatment for systemic lupus erythematosus if the mammal contains the cells and classifying the mammal as not being likely to respond to an anti-IFN treatment for systemic lupus erythematosus if the mammal does not contain the cells. The mammal can be a human. The one or more control mammals can be healthy humans. The cells and the control cells can be peripheral blood mononuclear cells. The method can include determining whether or not the mammal contains cells that express at least 5 of the genes or at least 10 of the genes to an extent greater than or less than the level of expression exhibited in the control cells. The extent can be greater than or less than the average level of expression exhibited in control cells from at least 10 control mammals or from at least 20 control mammals. The determining step can include measuring the level of mRNA expressed from at least 2 of the genes or from at least 5 of the genes.

In yet another aspect, this document features a method for assessing effectiveness of a treatment for systemic lupus erythematosus. The method comprises, or consists essentially of, determining whether or not a mammal having systemic lupus erythematosus disease and having received a treatment for the systemic lupus erythematosus disease contains cells having an IFN signature 1, an activity signature 1, an activity signature 2, or an activity signature 3 to a level less than that observed prior to the treatment, wherein the presence of the cells indicates that the treatment is effective. The mammal can be a human. The cells can be peripheral blood mononuclear cells. The IFN signature 1 can comprise, or consist essentially of, at least 10, 20, 30, 40, 50, 60, 70, 80, 90, 95, or 100 percent of the genes listed in Table 5. The activity signature 1 can comprise, or consist essentially of, at least 10, 20, 30, 40, 50, 60, 70, 80, 90, 95, or 100 percent of the genes listed in Table 16. The activity signature 2 can comprise, or consist essentially of, at least 10, 20, 30, 40, 50, 60, 70, 80, 90, 95, or 100 percent of the genes listed in Table 17. The activity signature 3 can comprise, or consist essentially of, at least 10, 20, 30, 40, 50, 60, 70, 80, 90, 95, or 100 percent of the genes listed in Table 19.

In yet another aspect, this document features a method for assessing effectiveness of a treatment for systemic lupus erythematosus. The method comprises, or consists essentially of, determining whether or not a mammal having systemic lupus erythematosus disease and having received a treatment for the systemic lupus erythematosus disease contains cells that express at least 2 of the genes listed in Table 5, 7, 9, 16, 17, or 19 to an extent greater than or less than the average level of expression exhibited in cells obtained from the mammal prior to the treatment, where the presence of the cells indicates that the treatment is effective. The mammal can be a human. The cells can be peripheral blood mononuclear cells. The method can include determining whether or not the mammal contains cells that express at least 5 of the genes or at least 10 of the genes to an extent greater than or less than the level of expression exhibited in the cells obtained from the mammal prior to the treatment. The determining step can include measuring the level of mRNA expressed from at least 2 of the genes or from at least 5 of the genes.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 5A shows the percentage of patients exhibiting the indicated clinical features in group 3 (ribosomal/mitochondrial positive, IFN positive, nuclear/transcription negative) vs. all other groups. FIG. 5B shows the percentage of patients exhibiting the indicated clinical features in the indicated combinations of groups vs. all other groups. CVA, cerebrovascular accident. LFT, liver function test.

FIG. 6A is a summary of the signatures defining the four SLE subgroups described herein. IFN, interferon; R/M, ribosomal/mitochondrial; N/T, nuclear/transcription. FIGS. 6B, 6C, 6D, and 6E are graphs showing clinical features associated with a subset of IFN signature positive patients. The frequency of selected clinical manifestations in each SLE subgroup is presented as the percentage of patients in the indicated subgroup. P-values were derived from a chi-square test comparing the frequency in the indicated subgroup vs. the frequency in all other subgroups combined. For FIG. 6E, the p-value represents comparison of groups 0 and 2 combined vs. all other patients.

DETAILED DESCRIPTION

Figure 1:
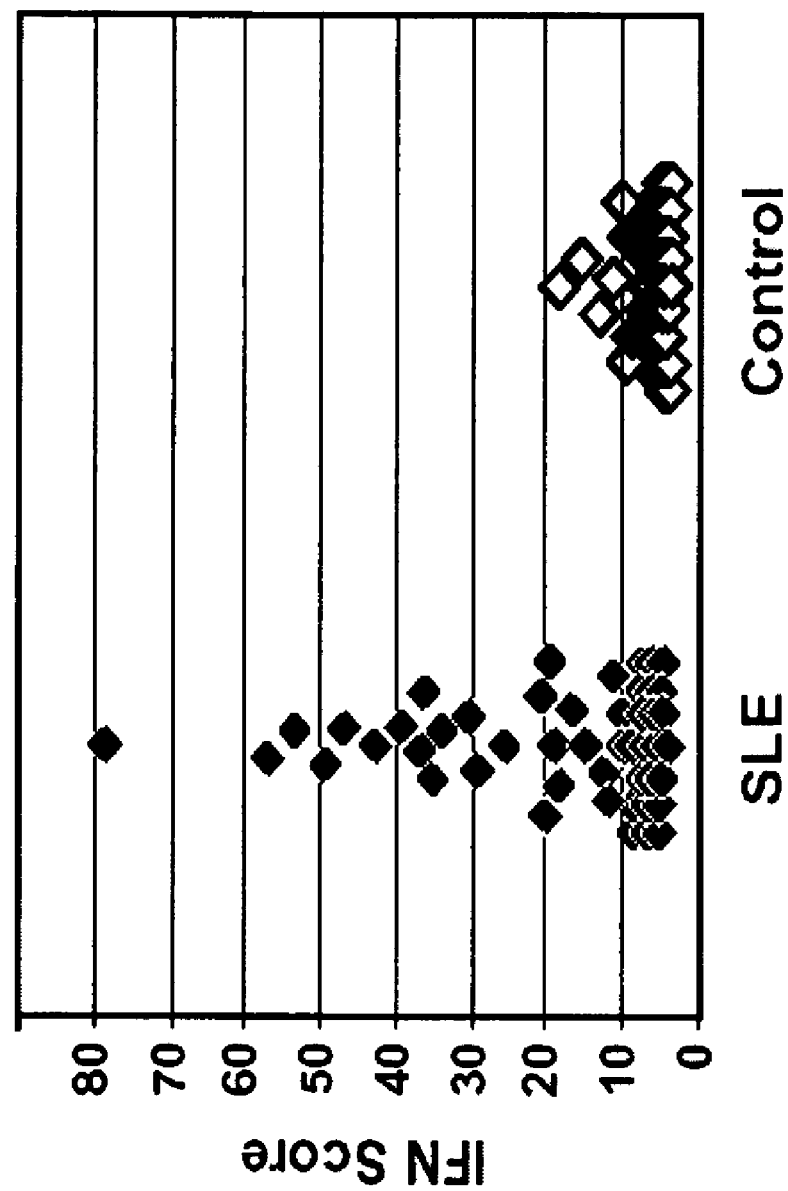
FIG. 1 is a graph plotting the IFN scores that were calculated for SLE patients and control subjects using the normalized expression levels of the 14 IFN-regulated genes that comprise the IFN signature; $p=2.8 \times 10^{-7}$.

This document provides methods and materials involved in diagnosing SLE such as methods and materials involved in diagnosing SLE, diagnosing severe SLE, and assessing a mammal's susceptibility to develop severe SLE. For example, this document provides nucleic acid arrays that can be used to diagnose SLE, severe SLE, and/or SLE-AIP in a mammal. Such arrays can allow clinicians to diagnose SLE, severe SLE, and/or SLE-AIP based on a determination of the expression levels of many genes that are differentially expressed. In addition, the methods and materials provided herein can be used to assess SLE activity, determine the likelihood of experiencing active SLE, and detect SLE treatment effectiveness.

1. Diagnosing SLE

This document provides methods for diagnosing a mammal (e.g., a human) as having SLE. In one embodiment, a mammal can be diagnosed as having SLE if it is determined that the mammal contains cells that express one or more of the genes listed in Table 1 or Tables 5, 7, 8, and 9 at a level that is greater or less than the average level of expression of the same one or more genes observed in control cells obtained from control mammals. In another embodiment, a mammal can be diagnosed as having SLE if it is determined that the mammal contains cells that express one or more of the genes listed in Table 2 or in Table 7 at a level that is greater than the average level of expression of the same one or more genes observed in control cells obtained from control mammals. In yet another embodiment, a mammal can be diagnosed as having SLE if it is determined that the mammal contains cells that express one or more of the genes listed in Table 3 or Table 8 at a level that is less than the average level of expression of the same one or more genes observed in control cells obtained from control mammals.

The mammal can be any mammal such as a human, dog, mouse, or rat. Any cell type can be isolated and evaluated. For example, peripheral blood mononuclear cells (PMBC), total white blood cells, lymph node cells, spleen cells, or tonsil cells can be isolated from a human patient and evaluated to determine if that patient contains cells that (1) express one or more of the genes listed in Table 1 or Tables 5, 7, 8, and 9 at a level that is greater or less than the average level of expression observed in control cells, (2) express one or more of the genes listed in Table 2 or in Table 7 at a level that is greater than the average level of expression observed in control cells, or (3) express one or more of the genes listed in Table 3 or Table 8 at a level that is less than the average level of expression observed in control cells. The expression of any number of the genes listed in Tables 1, 2, 3, 5, 7, 8, or 9 can be evaluated to diagnose SLE. For example, the expression of one or more than one (e.g., two, three, four, five, six, seven, eight, nine, ten, 15, 20, 25, 30, or more than 30) of the genes listed in Table 1, 2, 3, 5, 7, 8, or 9 can be used. Examples of gene combinations that can be evaluated include, without limitation, SP100 and FLJ11000; N1-acetyltransferase and RPS10; RPL39 and COX6A1; RPS3A, ATP5L and TIMM10; KIAA0471 and SFRS protein kinase 2; metallothionein 1F, COX7C, RPL9, and KIAA0876 protein; and torsin B, STAT1, UQCR, and IL6R.

The expression level can be greater than or less than the average level observed in control cells obtained from control mammals. Typically, a gene can be classified as being expressed at a level that is greater than or less than the average level observed in control cells if the expression levels differ by at least 1-fold (e.g., 1.5-fold, 2-fold, 3-fold, or more than 3-fold). In addition, the control cells typically are the same type of cells as those isolated from the mammal being evaluated. In some cases, the control cells can be isolated from one or more mammals that are from the same species as the mammal being evaluated. When diagnosing SLE, the control cells can be isolated from healthy mammals such as healthy humans who do not have SLE. Any number of control mammals can be used to obtain the control cells. For example, control cells can be obtained from one or more healthy mammals (e.g., at least 5, at least 10, at least 15, at least 20, or more than 20 control mammals).

Any method can be used to determine whether or not a specific gene is expressed at a level that is greater or less than the average level of expression observed in control cells. For example, the level of expression from a particular gene can be measured by assessing the level of mRNA expression from the gene. Levels of mRNA expression can be evaluated using, without limitation, northern blotting, slot blotting, quantitative reverse transcriptase polymerase chain reaction (RT-PCR), or chip hybridization techniques. Methods for chip hybridization assays include, without limitation, those described herein. Such methods can be used to determine simultaneously the relative expression levels of multiple mRNAs. Alternatively, the level of expression from a particular gene can be measured by assessing polypeptide levels. Polypeptide levels can be measured using any method such as immuno-based assays (e.g., ELISA), western blotting, protein arrays, or silver staining.

TABLE 1

Genes with expression levels that differ between SLE patients and normal controls

| Accession No. | Gene |
| --- | --- |
| U60060 | fasciculation and elongation protein zeta 1 (zygin I) |
| AF057036 | collagen-like tail subunit (single strand of homotrimer) of asymmetric acetylcholinesterase |
| M93107 | 3-hydroxybutyrate dehydrogenase (heart, mitochondrial) |
| U14575 | protein phosphatase 1, regulatory (inhibitor) subunit 8 |
| X15882 | collagen VI alpha-2 C-terminal globular domain |
| S68805 | glycine amidinotransferase (L-arginine: glycine amidinotransferase) |
| U75744 | deoxyribonuclease I-like 3 |
| AF091071 | similar to S. cerevisiae RER1 |
| AI651806 | cysteine-rich motor neuron 1 |
| AB028994 | KIAA1071 protein |
| S75168 | megakaryocyte-associated tyrosine kinase |
| X73617 | T cell receptor delta locus |
| X07730 | kallikrein 3, (prostate specific antigen) |
| AF009787 | T cell receptor beta locus |
| M21624 | T cell receptor delta locus |
| AB009598 | beta-1,3-glucuronyltransferase 3 (glucuronosyltransferase I) |
| AL021154 | E2F transcription factor 2 |
| L25444 | TAF6 RNA polymerase II, TATA box binding protein (TBP)-associated factor, 80 kD |
| AJ001383 | lymphocyte antigen 94 homolog, activating NK-receptor; NK-p46, (mouse) |
| U75370 | polymerase (RNA) mitochondrial (DNA directed) |
| AL049365 | DKFZp586A0618 |
| M16801 | nuclear receptor subfamily 3, group C, member 2 |
| M28827 | CD1C antigen, c polypeptide |
| U51712 | hypothetical protein SMAP31 |
| X66079 | Spi-B transcription factor (Spi-1/PU.1 related) |
| U11276 | killer cell lectin-like receptor subfamily B, member 1 |
| M36881 | lymphocyte-specific protein tyrosine kinase |
| M31523 | transcription factor 3 (E2A immunoglobulin enhancer binding factors E12/E47) |
| M26062 | interleukin 2 receptor, beta |
| AF026031 | putative mitochondrial outer membrane protein import receptor |
| AB011115 | KIAA0543 protein |
| AF041261 | leukocyte immunoglobulin-like receptor, subfamily A (without TM domain), member 4 |
| D55716 | MCM7 minichromosome maintenance deficient 7 (S. cerevisiae) |
| L04282 | zinc finger protein 148 (pHZ-52) |
| AJ001687 | DNA segment on chromosome 12 (unique) 2489 expressed sequence |
| AI524873 | like mouse brain protein E46 |
| U76421 | adenosine deaminase, RNA-specific, B1 (homolog of rat RED1) |
| AF031137 | lymphocyte antigen 117 |
| X59871 | transcription factor 7 (T-cell specific, HMG-box) |
| U43408 | tyrosine kinase, non-receptor, 1 |
| AB018289 | KIAA0746 protein |

TABLE 1-continued

Genes with expression levels that differ between SLE patients and normal controls

| Accession No. | Gene |
|---|---|
| AI761647 | IMAGE-2370113 |
| M18737 | granzyme A (granzyme 1, cytotoxic T-lymphocyte-associated serine esterase 3) |
| AB023220 | ubiquitin specific protease 20 |
| W26633 | melanoma antigen, family D, 1 |
| M68892 | integrin, beta 7 |
| AJ236885 | zinc finger protein 148 (pHZ-52) |
| L13858 | son of sevenless (*Drosophila*) homolog 2 |
| AF094481 | CGG triplet repeat binding protein 1 |
| M28215 | RAB5A, member RAS oncogene family |
| U43083 | guanine nucleotide binding protein (G protein), q polypeptide |
| X02344 | tubulin, beta, 2 |
| M22324 | alanyl (membrane) aminopeptidase (aminopeptidase N, aminopeptidase M, microsomal aminopeptidase, CD13, p150) |
| Y07566 | Ric-like, expressed in many tissues (*Drosophila*) |
| U50553 | DEAD/H (Asp-Glu-Ala-Asp/His) box polypeptide 3 |
| X54134 | protein tyrosine phosphatase, receptor type, E |
| L40388 | thyroid receptor interacting protein 15 |
| L19872 | aryl hydrocarbon receptor |
| U78107 | N-ethylmaleimide-sensitive factor attachment protein, gamma |
| AL050272 | DKFZP566B183 protein |
| U56998 | cytokine-inducible kinase |
| AI189226 | RAB31, member RAS oncogene family |
| Z50781 | delta sleep inducing peptide, immunoreactor |
| S87759 | protein phosphatase 1A (formerly 2C), magnesium-dependent, alpha isoform |
| U88629 | ELL-RELATED RNA POLYMERASE II, ELONGATION FACTOR |
| AF006513 | chromodomain helicase DNA binding protein 1 |
| AI138605 | hypothetical protein DKFZp566A1524 |
| L16794 | MADS box transcription enhancer factor 2, polypeptide D (myocyte enhancer factor 2D) |
| AL080235 | Ras-induced senescence 1 |
| L17418 | complement component (3b/4b) receptor 1, including Knops blood group system |
| Y00816 | complement component (3b/4b) receptor 1, including Knops blood group system |
| M63835 | Fc fragment of IgG, high affinity Ia, receptor for (CD64) |
| L13943 | glycerol kinase |
| U89278 | early development regulator 2 (homolog of polyhomeotic 2) |
| U58334 | tumor protein p53 binding protein, 2 |
| X54134 | protein tyrosine phosphatase, receptor type, E |
| X59834 | glutamate-ammonia ligase (glutamine synthase) |
| AL047596 | capicua homolog (*Drosophila*) |
| AB023211 | peptidyl arginine deiminase, type II |
| D43945 | transcription factor EC |
| U79273 | clone 23933 |
| Z18956 | solute carrier family 6 (neurotransmitter transporter, taurine), member 6 |
| Y10313 | interferon-related developmental regulator 1 |
| AF004849 | homeodomain interacting protein kinase 3 |
| AI808958 | KIAA0870 protein |
| U47634 | tubulin, beta, 4 |
| X55988 | ribonuclease, RNase A family, 2 (liver, eosinophil-derived neurotoxin) |
| W29030 | CGI-49 protein |
| U12471 | thrombospondin-1 |
| AF013591 | sudD (suppressor of bimD6, *Aspergillus nidulans*) homolog |
| X52015 | interleukin 1 receptor antagonist |
| M16967 | coagulation factor V (proaccelerin, labile factor) |
| U57094 | RAB27A, member RAS oncogene family |
| U66711 | lymphocyte antigen 6 complex, locus E |
| AA521060 | IMAGE-826408 |
| X68090 | IgG Fc receptor class IIA |
| Y08136 | acid sphingomyelinase-like phosphodiesterase |
| AL049685 | hypothetical protein similar to small G proteins, especially RAP-2A |
| L28957 | phosphate cytidylyltransferase 1, choline, alpha isoform |
| Z22576 | CD69 antigen (p60, early T-cell activation antigen) |
| U41766 | a disintegrin and metalloproteinase domain 9 (meltrin gamma) |
| M57230 | interleukin 6 signal transducer (gp130, oncostatin M receptor) |
| X17094 | paired basic amino acid cleaving enzyme (furin, membrane associated receptor protein) |
| AC005192 | interferon-related developmental regulator 1 |
| AI547258 | metallothionein 2A |
| L22075 | guanine nucleotide binding protein (G protein), alpha 13 |
| U22431 | hypoxia-inducible factor 1, alpha subunit (basic helix-loop-helix transcription factor) |
| AB006746 | phospholipid scramblase 1 |
| AF030196 | stannin |
| AA010078 | H4 histone family, member D |
| X56807 | desmocollin 2 |
| AL080156 | DKFZP434J214 protein |
| AF017257 | v-ets erythroblastosis virus E26 oncogene homolog 2 (avian) |
| AL049340 | DKFZp564P056 |
| M24283 | intercellular adhesion molecule 1 (CD54), human rhinovirus receptor |
| D49817 | 6-phosphofructo-2-kinase/fructose-2,6-biphosphatase 3 |
| AF016903 | agrin |
| U77914 | jagged 1 (Alagille syndrome) |
| M33882 | myxovirus (influenza) resistance 1, homolog of murine (interferon-inducible protein p78) |
| U68385 | Meis1, myeloid ecotropic viral integration site 1 homolog 3 (mouse) |
| L05515 | cAMP response element-binding protein CRE-BPa |
| U15555 | serine palmitoyltransferase, long chain base subunit 2 |
| L42025 | HIV-1 Rev binding protein |
| X07834 | superoxide dismutase 2, mitochondrial |
| D90144 | small inducible cytokine A3 |
| M13755 | interferon-stimulated protein, 15 kDa |
| M83670 | carbonic anhydrase IV |
| M55047 | synaptotagmin I |
| U91512 | ninjurin 1 |
| AB008775 | aquaporin 9 |
| X79535 | tubulin, beta polypeptide |
| J04102 | v-ets erythroblastosis virus E26 oncogene homolog 2 (avian) |
| D10040 | fatty-acid-Coenzyme A ligase, long-chain 2 |
| AW044649 | sin3-associated polypeptide, 30 kD |
| X03473 | H1 histone family, member 0 |
| AB007448 | solute carrier family 22 (organic cation transporter), member 4 |
| Z14138 | mitogen-activated protein kinase kinase kinase 8 |
| X02419 | uPA |
| U10473 | UDP-Gal: betaGlcNAc beta 1,4-galactosyltransferase, polypeptide 1 |
| AI679353 | solute carrier family 11 (proton-coupled divalent metal ion transporters), member 1 |
| AA203213 | interferon-stimulated protein, 15 kDa |
| AB018259 | KIAA0716 gene product |
| AF055993 | sin3-associated polypeptide, 30 kD |
| X54486 | serine (or cysteine) proteinase inhibitor, clade G (C1 inhibitor), member 1 |
| AJ225089 | 2'-5'-oligoadenylate synthetase-like |
| AL022318 | similar to APOBEC1 |
| S59049 | regulator of G-protein signalling 1 |
| Y10032 | serum/glucocorticoid regulated kinase |
| AI924594 | tetraspan 2 |
| D21205 | zinc finger protein 147 (estrogen-responsive finger protein) |
| U37707 | membrane protein, palmitoylated 3 (MAGUK p55 subfamily member 3) |
| L40387 | 2'-5'-oligoadenylate synthetase-like |
| X78711 | glycerol kinase |
| D10923 | putative chemokine receptor; GTP-binding protein |
| AW006742 | IMAGE-2489058 |
| AL109730 | EUROIMAGE 68600 |
| X99699 | XIAP associated factor-1 |
| AB000115 | hypothetical protein, expressed in osteoblast |
| L13210 | lectin, galactoside-binding, soluble, 3 binding protein |

TABLE 1-continued

Genes with expression levels that differ between SLE patients and normal controls

| Accession No. | Gene |
|---|---|
| U22970 | interferon, alpha-inducible protein (clone IFI-6-16) |
| U96721 | Hermansky-Pudlak syndrome |
| L10126 | activin A receptor, type IB |
| S62138 | TLS/CHOP |
| M33684 | protein tyrosine phosphatase, non-receptor type 1 |
| M63978 | vascular endothelial growth factor |
| X89101 | tumor necrosis factor receptor superfamily, member 6 |
| M60278 | diphtheria toxin receptor (heparin-binding epidermal growth factor-like growth factor) |
| X59770 | interleukin 1 receptor, type II |
| X04500 | interleukin 1, beta |
| D30783 | epiregulin |
| U43774 | Fc fragment of IgA, receptor for |

TABLE 2

Genes from Table 1 that are higher in SLE patients as compared to controls

| Accession No. | Gene |
|---|---|
| L13858 | son of sevenless (*Drosophilia*) homolog 2 |
| AF094481 | CGG triplet repeat binding protein 1 |
| M28215 | RAB5A, member RAS oncogene family |
| U43083 | guanine nucleotide binding protein (G protein), q polypeptide |
| X02344 | tubulin, beta, 2 |
| M22324 | alanyl (membrane) aminopeptidase (aminopeptidase N, aminopeptidase M, microsomal aminopeptidase, CD13, p150) |
| Y07566 | Ric-like, expressed in many tissues (*Drosophila*) |
| U50553 | DEAD/H (Asp-Glu-Ala-Asp/His) box polypeptide 3 |
| X54134 | protein tyrosine phosphatase, receptor type, E |
| L40388 | thyroid receptor interacting protein 15 |
| L19872 | aryl hydrocarbon receptor |
| U78107 | N-ethylmaleimide-sensitive factor attachment protein, gamma |
| AL050272 | DKFZP566B183 protein |
| U56998 | cytokine-inducible kinase |
| AI189226 | RAB31, member RAS oncogene family |
| Z50781 | delta sleep inducing peptide, immunoreactor |
| S87759 | protein phosphatase 1A (formerly 2C), magnesium-dependent, alpha isoform |
| U88629 | ELL-RELATED RNA POLYMERASE II, ELONGATION FACTOR |
| AF006513 | chromodomain helicase DNA binding protein 1 |
| AI138605 | hypothetical protein DKFZp566A1524 |
| L16794 | MADS box transcription enhancer factor 2, polypeptide D (myocyte enhancer factor 2D) |
| AL080235 | Ras-induced senescence 1 |
| L17418 | complement component (3b/4b) receptor 1, including Knops blood group system |
| Y00816 | complement component (3b/4b) receptor 1, including Knops blood group system |
| M63835 | Fc fragment of IgG, high affinity Ia, receptor for (CD64) |
| L13943 | glycerol kinase |
| U89278 | early development regulator 2 (homolog of polyhomeotic 2) |
| U58334 | tumor protein p53 binding protein, 2 |
| X54134 | protein tyrosine phosphatase, receptor type, E |
| X59834 | glutamate-ammonia ligase (glutamine synthase) |
| AL047596 | capicua homolog (*Drosophila*) |
| AB023211 | peptidyl arginine deiminase, type II |
| D43945 | transcription factor EC |
| U79273 | clone 23933 |
| Z18956 | solute carrier family 6 (neurotransmitter transporter, taurine), member 6 |
| Y10313 | interferon-related developmental regulator 1 |
| AF004849 | homeodomain interacting protein kinase 3 |
| AI808958 | KIAA0870 protein |
| U47634 | tubulin, beta, 4 |

TABLE 2-continued

Genes from Table 1 that are higher in SLE patients as compared to controls

| Accession No. | Gene |
|---|---|
| X55988 | ribonuclease, RNase A family, 2 (liver, eosinophil-derived neurotoxin) |
| W29030 | CGI-49 protein |
| U12471 | thrombospondin-1 |
| AF013591 | sudD (suppressor of bimD6, *Aspergillus nidulans*) homolog |
| X52015 | interleukin 1 receptor antagonist |
| M16967 | coagulation factor V (proaccelerin, labile factor) |
| U57094 | RAB27A, member RAS oncogene family |
| U66711 | lymphocyte antigen 6 complex, locus E |
| AA521060 | IMAGE-826408 |
| X68090 | IgG Fc receptor class IIA |
| Y08136 | acid sphingomyelinase-like phosphodiesterase |
| AL049685 | hypothetical protein similar to small G proteins, especially RAP-2A |
| L28957 | phosphate cytidylyltransferase 1, choline, alpha isoform |
| Z22576 | CD69 antigen (p60, early T-cell activation antigen) |
| U41766 | a disintegrin and metalloproteinase domain 9 (meltrin gamma) |
| M57230 | interleukin 6 signal transducer (gp130, oncostatin M receptor) |
| X17094 | paired basic amino acid cleaving enzyme (furin, membrane associated receptor protein) |
| AC005192 | interferon-related developmental regulator 1 |
| AI547258 | metallothionein 2A |
| L22075 | guanine nucleotide binding protein (G protein), alpha 13 |
| U22431 | hypoxia-inducible factor 1, alpha subunit (basic helix-loop-helix transcription factor) |
| AB006746 | phospholipid scramblase 1 |
| AF030196 | stannin |
| AA010078 | H4 histone family, member D |
| X56807 | desmocollin 2 |
| AL080156 | DKFZP434J214 protein |
| AF017257 | v-ets erythroblastosis virus E26 oncogene homolog 2 (avian) |
| AL049340 | DKFZp564P056 |
| M24283 | intercellular adhesion molecule 1 (CD54), human rhinovirus receptor |
| D49817 | 6-phosphofructo-2-kinase/fructose-2,6-biphosphatase 3 |
| AF016903 | agrin |
| U77914 | jagged 1 (Alagille syndrome) |
| M33882 | myxovirus (influenza) resistance 1, homolog of murine (interferon-inducible protein p78) |
| U68385 | Meis1, myeloid ecotropic viral integration site 1 homolog 3 (mouse) |
| L05515 | cAMP response element-binding protein CRE-BPa |
| U15555 | serine palmitoyltransferase, long chain base subunit 2 |
| L42025 | HIV-1 Rev binding protein |
| X07834 | superoxide dismutase 2, mitochondrial |
| D90144 | small inducible cytokine A3 |
| M13755 | interferon-stimulated protein, 15 kDa |
| M83670 | carbonic anhydrase IV |
| M55047 | synaptotagmin I |
| U91512 | ninjurin 1 |
| AB008775 | aquaporin 9 |
| X79535 | tubulin, beta polypeptide |
| J04102 | v-ets erythroblastosis virus E26 oncogene homolog 2 (avian) |
| D10040 | fatty-acid-Coenzyme A ligase, long-chain 2 |
| AW044649 | sin3-associated polypeptide, 30 kD |
| X03473 | H1 histone family, member 0 |
| AB007448 | solute carrier family 22 (organic cation transporter), member 4 |
| Z14138 | mitogen-activated protein kinase kinase kinase 8 |
| X02419 | uPA |
| U10473 | UDP-Gal: betaGlcNAc beta 1,4-galactosyltransferase, polypeptide 1 |
| AI679353 | solute carrier family 11 (proton-coupled divalent metal ion transporters), member 1 |
| AA203213 | interferon-stimulated protein, 15 kDa |
| AB018259 | KIAA0716 gene product |
| AF055993 | sin3-associated polypeptide, 30 kD |
| X54486 | serine (or cysteine) proteinase inhibitor, clade G (C1 inhibitor), member 1 |

TABLE 2-continued

Genes from Table 1 that
are higher in SLE patients as compared to controls

| Accession No. | Gene |
|---|---|
| AJ225089 | 2'-5'-oligoadenylate synthetase-like |
| AL022318 | similar to APOBEC1 |
| S59049 | regulator of G-protein signalling 1 |
| Y10032 | serum/glucocorticoid regulated kinase |
| AI924594 | tetraspan 2 |
| D21205 | zinc finger protein 147 (estrogen-responsive finger protein) |
| U37707 | membrane protein, palmitoylated 3 (MAGUK p55 subfamily member 3) |
| L40387 | 2'-5'-oligoadenylate synthetase-like |
| X78711 | glycerol kinase |
| D10923 | putative chemokine receptor; GTP-binding protein |
| AW006742 | IMAGE-2489058 |
| AL109730 | EUROIMAGE 68600 |
| X99699 | XIAP associated factor-1 |
| AB000115 | hypothetical protein, expressed in osteoblast |
| L13210 | lectin, galactoside-binding, soluble, 3 binding protein |
| U22970 | interferon, alpha-inducible protein (clone IFI-6-16) |
| U96721 | Hermansky-Pudlak syndrome |
| L10126 | activin A receptor, type IB |
| S62138 | TLS/CHOP |
| M33684 | protein tyrosine phosphatase, non-receptor type 1 |
| M63978 | vascular endothelial growth factor |
| X89101 | tumor necrosis factor receptor superfamily, member 6 |
| M60278 | diphtheria toxin receptor (heparin-binding epidermal growth factor-like growth factor) |
| X59770 | interleukin 1 receptor, type II |
| X04500 | interleukin 1, beta |
| D30783 | epiregulin |
| U43774 | Fc fragment of IgA, receptor for |

TABLE 3

Genes from Table 1 that
are lower in SLE patients as compared to controls

| Accession No. | Gene |
|---|---|
| U60060 | fasciculation and elongation protein zeta 1 (zygin I) |
| AF057036 | collagen-like tail subunit (single strand of homotrimer) of asymmetric acetylcholinesterase |
| M93107 | 3-hydroxybutyrate dehydrogenase (heart, mitochondrial) |
| U14575 | protein phosphatase 1, regulatory (inhibitor) subunit 8 |
| X15882 | collagen VI alpha-2 C-terminal globular domain |
| S68805 | glycine amidinotransferase (L-arginine: glycine amidinotransferase) |
| U75744 | deoxyribonuclease I-like 3 |
| AF091071 | similar to S. cerevisiae RER1 |
| AI651806 | cysteine-rich motor neuron 1 |
| AB028994 | KIAA1071 protein |
| S75168 | megakaryocyte-associated tyrosine kinase |
| X73617 | T cell receptor delta locus |
| X07730 | kallikrein 3, (prostate specific antigen) |
| AF009787 | T cell receptor beta locus |
| M21624 | T cell receptor delta locus |
| AB009598 | beta-1,3-glucuronyltransferase 3 (glucuronosyltransferase I) |
| AL021154 | E2F transcription factor 2 |
| L25444 | TAF6 RNA polymerase II, TATA box binding protein (TBP)-associated factor, 80 kD |
| AJ001383 | lymphocyte antigen 94 homolog, activating NK-receptor; NK-p46, (mouse) |
| U75370 | polymerase (RNA) mitochondrial (DNA directed) |
| AL049365 | DKFZp586A0618 |
| M16801 | nuclear receptor subfamily 3, group C, member 2 |
| M28827 | CD1C antigen, c polypeptide |
| U51712 | hypothetical protein SMAP31 |
| X66079 | Spi-B transcription factor (Spi-1/PU.1 related) |
| U11276 | killer cell lectin-like receptor subfamily B, member 1 |

TABLE 3-continued

Genes from Table 1 that
are lower in SLE patients as compared to controls

| Accession No. | Gene |
|---|---|
| M36881 | lymphocyte-specific protein tyrosine kinase |
| M31523 | transcription factor 3 (E2A immunoglobulin enhancer binding factors E12/E47) |
| M26062 | interleukin 2 receptor, beta |
| AF026031 | putative mitochondrial outer membrane protein import receptor |
| AB011115 | KIAA0543 protein |
| AF041261 | leukocyte immunoglobulin-like receptor, subfamily A (without TM domain), member 4 |
| D55716 | MCM7 minichromosome maintenance deficient 7 (S. cerevisiae) |
| L04282 | zinc finger protein 148 (pHZ-52) |
| AJ001687 | DNA segment on chromosome 12 (unique) 2489 expressed sequence |
| AI524873 | like mouse brain protein E46 |
| U76421 | adenosine deaminase, RNA-specific, B1 (homolog of rat RED1) |
| AF031137 | lymphocyte antigen 117 |
| X59871 | transcription factor 7 (T-cell specific, HMG-box) |
| U43408 | tyrosine kinase, non-receptor, 1 |
| AB018289 | KIAA0746 protein |
| AI761647 | IMAGE-2370113 |
| M18737 | granzyme A (granzyme 1, cytotoxic T-lymphocyte-associated serine esterase 3) |
| AB023220 | ubiquitin specific protease 20 |
| W26633 | melanoma antigen, family D, 1 |
| M68892 | integrin, beta 7 |
| AJ236885 | zinc finger protein 148 (pHZ-52) |

2. Diagnosing Severe SLE and SLE-AIP

This document also provides methods for diagnosing a mammal (e.g., a human) as having severe SLE or SLE-AIP. In one embodiment, a mammal can be diagnosed as having severe SLE or SLE-AIP if it is determined that the mammal contains cells that express one or more of the genes listed in Table 4 or Table 5 at a level that is greater than or less than the average level of expression of the same one or more genes observed in control cells obtained from control mammals.

As described herein, the mammal can be any mammal such as a human, dog, mouse, or rat. Any cell type can be isolated and evaluated. For example, peripheral blood mononuclear cells (PMBC), total white blood cells, lymph node cells, spleen cells, or tonsil cells can be isolated from a human patient and evaluated to determine if that patient contains cells that express one or more of the genes listed in Table 4 or Table 5 at a level that is greater than or less than the average level of expression observed in control cells. The expression of any number of the genes listed in Table 4 or Table 5 can be evaluated to diagnose severe SLE or SLE-AIP. For example, the expression of one or more than one (e.g., two, three, four, five, six, seven, eight, nine, ten, 11, 12, 13, or all 14) of the genes listed in Table 4 or Table 5 can be used. Examples of gene combinations that can be evaluated include, without limitation, biliverdin reductase A and metallothionein 2A; 2'-5'-OAS2 and SCO2; IFIT-3, IFN regulatory factor 7, and RNA helicase; leucine aminopeptidase, metallothionein 1E, and biliary glycoprotein; and AW474434, UBE2L6, IFIT-1, MX2, and hypothetical AL031602.

The expression level can be greater than or less than the average level observed in control cells obtained from control mammals. Typically, a gene can be classified as being expressed at a level that is greater than or less than the average level observed in control cells if the expression levels differ by at least 1-fold (e.g., 1.5-fold, 2-fold, 3-fold, or more than 3-fold). In addition, the control cells typically are the same type of cells as those isolated from the mammal being evaluated. In some cases, the control cells can be isolated from one or more mammals that are from the same species as the mammal being evaluated. When diagnosing severe SLE or SLE-AIP, the control cells can be isolated from mammals having mild SLE or from healthy mammals such as healthy humans who do not have SLE. Any number of control mammals can be used to obtain the control cells. For example, control cells can be obtained from one or more healthy mammals (e.g., at least 5, at least 10, at least 15, at least 20, or more than 20 control mammals).

TABLE 4

Genes with expression levels that differ between SLE patients having low and high IFN scores

| Accession No. | Gene |
| --- | --- |
| M63835 | Fc fragment of IgG, high affinity Ia, receptor for (CD64) |
| X54486 | serine (or cysteine) proteinase inhibitor, clade G (C1 inhibitor), member 1 |
| L13210 | lectin, galactoside-binding, soluble, 3 binding protein |
| M33882 | myxovirus (influenza) resistance 1, homolog of murine (interferon-inducible protein p78) |
| AA203213 | interferon-stimulated protein, 15 kDa |
| X99699 | XIAP associated factor-1 |
| AJ225089 | 2'-5'-oligoadenylate synthetase-like |
| U22970 | interferon, alpha-inducible protein (clone IFI-6-16) |
| AB000115 | Interferon-induced protein 44-like (hypothetical protein, expressed in osteoblast) |
| AL047596 | capicua homolog (Drosophila) |
| AB006746 | phospholipid scramblase 1 |
| AL022318 | APOBEC3B (similar to APOBEC1) |
| U66711 | lymphocyte antigen 6 complex, locus E |
| X55988 | ribonuclease, RNase A family, 2 (liver, eosinophil-derived neurotoxin) |

Any method can be used to determine whether or not a specific gene is expressed at a level that is greater or less than the average level of expression observed in control cells. For example, the level of expression from a particular gene can be measured by assessing the level of mRNA expression from the gene. Levels of mRNA expression can be evaluated using, without limitation, northern blotting, slot blotting, quantitative reverse transcriptase polymerase chain reaction (RT-PCR), or chip hybridization techniques. Methods for chip hybridization assays include, without limitation, those described herein. Such methods can be used to determine simultaneously the relative expression levels of multiple mRNAs. Alternatively, the level of expression from a particular gene can be measured by assessing polypeptide levels. Polypeptide levels can be measured using any method such as immuno-based assays (e.g., ELISA), western blotting, or silver staining.

3. Identifying Mammals Predisposed to Develop Severe SLE and SLE-AIP

This document also provides methods for diagnosing a mammal (e.g., a human) as being predisposed to develop severe SLE or SLE-AIP. In one embodiment, a mammal can be diagnosed as being predisposed to develop severe SLE or SLE-AIP if it is determined that the mammal contains cells that express one or more of the genes listed in Table 4 or Table 5 at a level that is greater than or less than the average level of expression of the same one or more genes observed in control cells obtained from control mammals.

As described herein, the mammal can be any mammal such as a human, dog, mouse, or rat. Any cell type can be isolated and evaluated. For example, peripheral blood mononuclear cells (PMBC), total white blood cells, lymph node cells, spleen cells, or tonsil cells can be isolated from a human patient and evaluated to determine if that patient contains cells that express one or more of the genes listed in Table 4 or Table 5 at a level that is greater than the average level of expression observed in control cells. The expression of any number of the genes listed in Table 4 or Table 5 can be evaluated to diagnose a mammal as being predisposed to develop severe SLE or SLE-AIP. For example, the expression of one or more than one (e.g., two, three, four, five, six, seven, eight, nine, ten, 11, 12, 13, or all 14) of the genes listed in Table 4 or Table 5 can be used. Examples of gene combinations that can be evaluated include, without limitation, those disclosed herein.

The expression level can be greater than or less than the average level observed in control cells obtained from control mammals. Typically, a gene can be classified as being expressed at a level that is greater than or less than the average level observed in control cells if the expression levels differ by at least 1-fold (e.g., 1.5-fold, 2-fold, 3-fold, or more than 3-fold). In addition, the control cells typically are the same type of cells as those isolated from the mammal being evaluated. In some cases, the control cells can be isolated from one or more mammals that are from the same species as the mammal being evaluated. When determining a mammal's susceptibility to develop severe SLE or SLE-AIP, the control cells can be isolated from mammals having mild SLE or from healthy mammals such as healthy humans who do not have SLE. Any number of control mammals can be used to obtain the control cells. For example, control cells can be obtained from one or more healthy mammals (e.g., at least 5, at least 10, at least 15, at least 20, or more than 20 control mammals).

Any method can be used to determine whether or not a specific gene is expressed at a level that is greater or less than the average level of expression observed in control cells. For example, the level of expression from a particular gene can be measured by assessing the level of mRNA expression from the gene. Levels of mRNA expression can be evaluated using, without limitation, northern blotting, slot blotting, quantitative reverse transcriptase polymerase chain reaction (RT-PCR), or chip hybridization techniques. Methods for chip hybridization assays include, without limitation, those described herein. Such methods can be used to determine simultaneously the relative expression levels of multiple mRNAs. Alternatively, the level of expression from a particular gene can be measured by assessing polypeptide levels. Polypeptide levels can be measured using any method such as immuno-based assays (e.g., ELISA), western blotting, or silver staining.

4. Diagnosing SLE Disease Activity

This document also provides methods and materials for diagnosing a mammal (e.g., a human) as having SLE disease activity. A number of measures can typically be used to define active SLE disease. Such disease activity measures include, without limitation, the SLE Disease Activity Index (SLE-DAI), a physician's global assessment (PGA), the Systemic Lupus Activity Measure (SLAM), the erythrocyte sedimentation rate (ESR), the white blood cell (WBC) count, and the hematocrit. A mammal can be diagnosed as having active or inactive SLE disease based on one or more disease activity measures. For example, a human having a PGA$\geq$1.5 and SLEDAI$\geq$3 can be diagnosed as having active SLE disease. In some cases, a human having a PGA$\leq$1 and SLEDAI$\leq$2 can be diagnosed as having inactive SLE disease.

In some embodiments, a mammal can be diagnosed as having active SLE disease if it is determined that the mammal contains cells that express one or more of the genes listed in Table 16, Table 17, or Table 19 at a level that is greater than or less than the average level of expression of the same one or more genes observed in control cells obtained from control mammals.

As described herein, the mammal can be any mammal, such as a human, dog, mouse, or rat. Any cell type can be isolated and evaluated. For example, peripheral blood mononuclear cells (PBMC), total white blood cells, lymph node cells, spleen cells, or tonsil cells can be isolated from a human patient and evaluated to determine if that patient contains cells that express one or more of the genes listed in Table 16, Table 17, or Table 19 at a level that is greater than or less than the average level of expression observed in control cells. The expression of any number of the genes listed in Table 16, Table 17, or Table 19 can be evaluated to diagnose SLE disease activity. For example, the expression of one or more than one (e.g., two, three, four, five, six, seven, eight, nine, ten, 25, 37, 50, 75, 100, 156, or all) of the genes listed in Table 16, Table 17, or Table 19 can be used. Examples of gene combinations that can be evaluated include, without limitation, Ig kappa constant, Ig lambda joining 3, thioredoxin domain containing 5, and interferon induced transmembrane protein 1; IgM VDJ-region, Ig lambda variable 3-21, Ig heavy constant mu, biliverdin reductase A, and CTD small phosphatase-li; and signal-transducing adaptor protein-2, motilin, and interferon-stimulated transcription factor 3, gamma 48 kDa.

The expression level can be greater than or less than the average level observed in control cells obtained from control mammals. Typically, a gene can be classified as being expressed at a level that is greater than or less than the average level observed in control cells if the expression levels differ by at least 1-fold (e.g., 1.5-fold, 2-fold, 3-fold, or more than 3-fold). In addition, the control cells typically are the same type of cells as those isolated from the mammal being evaluated. In some cases, the control cells can be isolated from one or more mammals that are from the same species as the mammal being evaluated. When diagnosing active SLE disease, the control cells can be isolated from mammals having inactive SLE or from healthy mammals, such as healthy humans who do not have SLE. Any number of control mammals can be used to obtain the control cells. For example, control cells can be obtained from one or more healthy mammals (e.g., at least 5, at least 10, at least 15, at least 20, or more than 20 control mammals).

Any method can be used to determine whether or not a specific gene is expressed at a level that is greater or less than the average level of expression observed in control cells. For example, the level of expression from a particular gene can be measured by assessing the level of mRNA expression from the gene. Levels of mRNA expression can be evaluated using, without limitation, real-time quantitative PCR, northern blotting, slot blotting, or microarray technology. Methods for microarray assays include, without limitation, those described herein. Such methods can be used to determine simultaneously the relative expression levels of multiple mRNAs. In some cases, the level of expression from a particular gene can be measured by assessing polypeptide levels. Polypeptide levels can be measured using any method such as immuno-based assays (e.g., ELISA), Western blotting, or protein arrays.

Once a mammal (e.g., a human) has been diagnosed as having active SLE disease, the mammal can be monitored over time for an increase or a decrease in SLE disease activity. For example, a mammal can be assessed as having an increased or decreased SLE disease activity if it is determined that the mammal contains cells that express one or more genes listed in Table 16, Table 17, or Table 19 at a level that is greater than or less than the average level of expression of the same one or more genes observed in cells obtained previously from the same mammal. A mammal can be monitored for SLE disease activity over any period of time with any frequency. For example, a mammal can be monitored every three months for one year or once a year for as long as the mammal is alive. In some cases, the SLE disease activity of a mammal can be monitored with a single follow-up assessment.

A mammal can also be monitored for SLE disease activity before, during, and after being treated for SLE. For example, a mammal can be monitored for SLE disease activity while being treated with anti-interferon therapy, hydroxychloroquinone, steroids, or immunosuppressive drugs. Monitoring a mammal for SLE disease activity during treatment of the mammal for SLE can allow the effectiveness of the SLE therapy to be assessed. For example, a decrease in SLE activity during or after treatment with an SLE therapy compared to the SLE activity before treatment with an SLE therapy can indicate that the SLE therapy is effective. Monitoring a mammal for SLE disease activity during treatment of the mammal for SLE can also allow responders to the SLE therapy to be identified. For example, a decrease in SLE activity in a mammal during treatment with an SLE therapy compared to the SLE activity in the mammal before treatment with the SLE therapy can indicate that the mammal is a responder to the SLE therapy.

5. Identifying Mammals Likely to Experience SLE Disease Activity

This document also provides methods and materials for identifying mammals (e.g., humans) that have SLE and are likely to experience SLE disease activity. For example, future SLE disease activity in a mammal can be predicted by determining whether or not the mammal contains cells that express one or more of the genes listed in Table 16, Table 17, or Table 19 at a level that is greater than or less than the average level of expression of the same one or more genes observed in control cells obtained from control mammals.

6. Identifying Mammals Likely to Respond to Anti-IFN Treatment

This document also provides methods and materials for identifying mammals (e.g., humans) likely to respond to an anti-IFN SLE treatment. For example, the methods and materials provided herein can be used to identify SLE patients with an IFN signature. Once identified, those patients can be treated with an anti-IFN treatment such as humanized anti-IFN antibodies. In some cases, the effectiveness of the anti-IFN SLE treatment can be monitored as described herein.

7. Arrays

This document also provides nucleic acid arrays. The arrays provided herein can be two-dimensional arrays, and can contain at least two different nucleic acid molecules (e.g., at least three, at least five, at least ten, at least 20, at least 30, at least 50, at least 100, or at least 200 different nucleic acid molecules). Each nucleic acid molecule can have any length. For example, each nucleic acid molecule can be between 10 and 250 nucleotides (e.g., between 12 and 200, 14 and 175, 15 and 150, 16 and 125, 18 and 100, 20 and 75, or 25 and 50 nucleotides) in length. In some cases, an array can contain one or more cDNA molecules encoding, for example, partial or entire polypeptides. In addition, each nucleic acid molecule can have any sequence. For example, the nucleic acid molecules of the arrays provided herein can contain sequences that are present within the genes listed in Tables 1, 2, 3, 4, 5, 7, 8, 9, 16, 17, and/or 19.

Typically, at least 25% (e.g., at least 30%, at least 40%, at least 50%, at least 60%, at least 75%, at least 80%, at least 90%, at least 95%, or 100%) of the nucleic acid molecules of an array provided herein contain a sequence that is (1) at least 10 nucleotides (e.g., at least 11, 12, 13, 14, 15, 16, 17, 18, 19, 20, 25, or more nucleotides) in length and (2) at least about 95 percent (e.g., at least about 96, 97, 98, 99, or 100) percent identical, over that length, to a sequence present within a gene listed in Tables 1, 2, 3, 4, 5, 7, 8, 9, 16, 17, and/or 19. For example, an array can contain 100 nucleic acid molecules located in known positions, where each of the 100 nucleic acid molecules is 100 nucleotides in length while containing a sequence that is (1) 30 nucleotides is length, and (2) 100 percent identical, over that 30 nucleotide length, to a sequence of one of the genes listed in Table 4. Thus, a nucleic acid molecule of an array provided herein can contain a sequence present within a gene listed in Tables 1, 2, 3, 4, 5, 7, 8, 9, 16, 17, and/or 19 where that sequence contains one or more (e.g., one, two, three, four, or more) mismatches.

The nucleic acid arrays provided herein can contain nucleic acid molecules attached to any suitable surface (e.g., plastic or glass). In addition, any method can be use to make a nucleic acid array. For example, spotting techniques and in situ synthesis techniques can be used to make nucleic acid arrays. Further, the methods disclosed in U.S. Pat. Nos. 5,744,305 and 5,143,854 can be used to make nucleic acid arrays.

The invention will be further described in the following examples, which do not limit the scope of the invention described in the claims.

EXAMPLES

Example 1

Identifying Genes That Can Be Used to Diagnose SLE

PBMCs were collected from 48 SLE patients and 42 healthy, age- and gender-matched control individuals. All patients had physician-verified SLE and met at least four of the eleven ACR criteria for lupus. The average age of SLE patients was 45±11 years, and the average age of controls was 34±13 years. Each PBMC sample contained monocytes/macrophages, B and T lymphocytes, and natural killer cells.

For the first 11 patients and 11 controls, poly $A^+$ mRNA was extracted from the collected PBMC samples. Briefly, 60 mL of peripheral blood was drawn into a heparinized syringe. Whole blood was layered over an equal volume of Histopaque and centrifuged at 400× g for 30 minutes at 25° C. Plasma was harvested and stored at −80° C. PBMCs were harvested and washed twice in 1× PBS, and the mRNA was isolated using a FastTrack mRNA isolation kit (Invitrogen, Carlsbad, Calif.).

For the next 37 patients and 31 controls, total RNA was extracted from the collected PBMC samples. Briefly, peripheral blood was drawn into CPT tubes (Becton-Dickinson, Franklin Lakes, N.J.), and plasma and PBMCs were collected according to manufacturer's protocol. Plasma was stored at −80° C., and total RNA was isolated from PBMCs using Trizol (Gibco-BRL, Invitrogen, Carlsbad, Calif.) followed by an RNeasy cleanup (Qiagen, Valencia, Calif.).

About 5 to 10 μg of total RNA or about 100-200 ng of poly $A^+$ RNA was used to prepare biotinylated cRNA for hybridization using the standard Affymetrix protocol (Expression Analysis Technical Manual, Affymetrix, Inc., 2000). Briefly, RNA was converted to first strand cDNA using a T7-linked oligo(dT) primer (Genset, La Jolla, Calif.) followed by second strand synthesis (Gibco-BRL). The dscDNA was then used as template for labeled in vitro transcription reactions using biotinylated ribonucleotides (Enzo, Farmingdale, N.Y.). Fifteen μg of each labeled cRNA was hybridized to Affymetrix U95A GeneChips (Affymetrix, Santa Clara, Calif.) using standard conditions in an Affymetrix fluidics station.

After chip hybridization and initial data analysis, the expression values for 10,260 genes represented on the chip were compared between SLE patients and controls using a non-paired Student's T-test.

Affymetrix Microarray Suite (MAS) 4.0 software was used to generate expression values (referred to as an "average difference;" AD) for each gene. Each chip was scaled to an overall intensity of 1500 to correct for minor differences in overall chip hybridization intensity and to allow comparison between chips. A threshold of 20 AD units was assigned to any gene that was called "Absent" by MAS. In addition, any gene with an AD less than 20 was assigned this threshold. Data from U95Av1 and U95Av2 chips were aligned by discarding the 51 probe sets that were not present on both chips. The analysis identified 161 unique genes that were differentially expressed using the following criteria: p<0.001, fold-change>1.5, mean expression value difference>100 units.

Despite the use of the same oligo(dT) primer for cDNA synthesis, consistent differences between the raw AD values obtained from poly$A^+$ RNA and total RNA samples were noted that were not corrected by chip scaling. Furthermore, each dataset (i.e., poly$A^+$ RNA and total RNA) showed similar differential gene expression between the respective groups of patients and controls. For example, the initial 11/11 dataset identified a larger than expected number of interferon-regulated genes. A gene-by-gene scaling approach thus was employed so that the two datasets could be combined and examined together. The scaling strategy was based on the assumption that the mean expression level (mean AD) of genes between the two control groups (total vs. poly$A^+$ RNA) should be equal. For each gene, the mean of the two control groups was compared to generate the gene-specific scaling factor. The poly$A^+$ samples were corrected by the scaling factor so that the means of the two control groups (total and poly$A^+$) were identical. This scaled dataset then was used for all subsequent analysis.

Identification of stress response genes: During the course of collecting and analyzing the various samples, it was determined that many genes in peripheral blood cells undergo striking stress responses following incubation ex vivo, even during somewhat limited periods of time (i.e., less than 1 hour). A formal experiment was designed and performed to identify those genes that were regulated by incubation of cells ex vivo. Changes in global gene expression were examined using whole blood after overnight shipment by a commercial carrier. This study utilized samples from eight healthy control individuals. Approximately 30 mL of blood was drawn into four CPT tubes. PBMCs were isolated from two tubes and resuspended in RNAlater (Ambion, Austin, Tex.). RNAlater immediately lyses the cells and protects the RNA from degradation, thus providing an accurate profile of gene expression immediately ex vivo. The RNA preserved in RNAlater and the two CPT tubes with whole blood were shipped by overnight carrier. Total RNA was extracted and prepared for hybridization as described above. Thus, global gene expression profiles were obtained from both a fresh blood sample and from blood shipped overnight, with both samples coming from the same blood draw.

Data were analyzed using MAS 4.0 and each chip was scaled to 1500. Absent and low expression values were assigned a threshold of 20 AD units as described above. A paired T-Test was used to compare the gene expression profiles of fresh blood vs. blood shipped by overnight carrier. Based on this experiment, 2076 genes were identified that displayed significant changes in expression under these environmental stresses (p<0.01). These genes, many of which are involved in various cell stress pathways, were excluded from further analysis due to the high level of variability that they exhibited.

Comparison analyses: The individual gene expression levels of SLE patients and controls were compared using an unpaired Student's T-test. Genes selected for further analysis met the following three criteria:

(i) p <0.001 by unpaired T-test, (ii) change in expression of at least 1.5-fold when comparing the means of the two groups, and (iii) difference in expression of at least 100 when comparing the means of the two groups.

Overall, 484 genes were differentially expressed at the p<0.001 level, while 178 genes were both differentially expressed at the p<0.001 level and showed mean AD values that differed by more than 1.5-fold. The final dataset of 161 individual genes (represented by 171 Genbank accession numbers) met all three criteria. These genes, which demonstrated differential expression between SLE patients and normal controls, are listed in Table 1.

Expression values for each of the 161 genes were converted to "fold-differences" by dividing each value by the mean of the control expression values. Unsupervised hierarchical clustering then was applied to the dataset. Hierarchical clustering was performed using Cluster and visualized using TreeView (M. Eisen, Stanford; available on the internet at rana.lbl.gov). This analysis identified gene expression patterns that differentiated most SLE patients from healthy controls. Thirty-seven of the 48 SLE patients clustered tightly together, while 11 of the patients co-clustered with controls. Six of the 42 control subjects clustered together with the large group of patients.

Most (124 of 161, 77%) of the genes that best distinguished SLE from control PBMCs were expressed at higher levels in SLE patients than in normal subjects. These are presented in Table 2. A number of these genes have known or suspected roles in the immune system. For example, many SLE patients were found to overexpress mRNA for the following cell surface markers: TNFR6 (Fas/CD95), a death receptor; ICAM-1 (CD54), an adhesion molecule; CD69, an activation antigen; and complement receptor 1. Of interest, three different Fc receptors were expressed at elevated levels: the Fc receptor for IgA (FCAR, CD89), and the IgG receptors FcRγIIA (CD32) and FcRγI (CD64). Three molecules in the inflammatory IL-1 cytokine pathway—IL-1β, the IL-1 receptor II (IL-1RII), and the IL-1 receptor antagonist—also were generally overexpressed. Interestingly, Jagged 1, a ligand for Notch 1 located in the SLE susceptibility interval on chromosome 20p, also was overexpressed in some patients. Other notable genes that were overexpressed in SLE patients include the signaling molecules MAP3K-8, RAB27, interleukin-6 signal transducer, the transcription factors v-ets 2, MADS box transcription factor 2, and the estrogen responsive zinc finger protein 147.

A number of genes were expressed at lower levels in patients than controls. These are presented in Table 3, and included T cell genes such as Lck, TCR delta, and TCR beta. Flow cytometry of freshly stained PBMCs was used to confirm that there was a T cell lymphopenia in many of the patients (i.e., about a 20% decrease, on average, in percentage of CD3$^+$ T cells). The patients also demonstrated a significant increase in the percentage of monocytes, as compared to the percentage of monocytes in controls. Specifically, PBMC populations from SLE patients (n=18) contained 52% T cells, 5% B cells, 28% monocytes/macrophages, and 15% NK cells. PMBC populations from control subjects (n=28) contained 65% T cells, 6% B cells, 13% monocytes/macrophages, and 16% NK cells. The percentages of T cells (p=0.014) and monocytes (p =0.00001) thus differed between SLE and controls. These differences in baseline cell populations clearly contribute to some of the differences in gene expression observed, and highlight the importance of documenting cell percentages in mixed cell populations.

Identification of IFN-regulated genes: One of the most striking mRNA clusters contained several genes previously identified as being interferon-regulated (Der et al. (1998) *Proc. Natl. Acad. Sci. U.S.A.* 95:15623). Interferons are highly active cytokines important for maintaining viral immunity (IFN-α and IFN-β) and for mediating TH1 immune responses (IFN-γ). Genes in this cluster were up-regulated in about half of the SLE patients, and were expressed at low levels in most of the control subjects.

Experiments were conducted to examine the extent to which the genes in this cluster could be regulated in PBMCs by IFN treatment in vitro. Peripheral blood was drawn from each of four healthy control individuals. PBMCs were isolated over Lymphocyte Separation Medium (Mediatech Cellgro, Hemdon, Va.) according to the manufacturer's protocol. After the last wash, cells were resuspended in complete media (RPMI1640, 10% heat inactivated FBS, 2 mM L-glutamine, pen/strep) at a final concentration of $2 \times 10^6$ cells/mL. PBMCs were cultured for six hours at 37° C. with the following additions:

(i) PBS+0.1 % BSA control, (ii) IFN-α and IFN-β (R&D Systems, Minneapolis, Minn.), each at 1000 U/mL in PBS+0.1% BSA, and (iii) IFN-γ (R&D Systems, Minneapolis, Minn.), 1000 U/mL in PBS+0.1% BSA.

Following the incubation, total RNA was isolated, and cRNA probes were prepared for chip hybridization. Data were analyzed using MAS 4.0 software, and all chips were scaled to 1500. Absent and low expression values were assigned a threshold of 20 AD units as described above. Genes that met both of the criteria below in all four experiments were identified as IFN-regulated:

(i) change in expression of at least 2-fold when compared to untreated control, and (ii) difference in expression of at least 500 AD units when compared to untreated control.

Changes in gene expression following IFN treatment were assessed relative to a six-hour control culture. This analysis identified 286 genes that demonstrated more than a 2-fold change in expression from baseline, and an absolute mean difference in the level of expression of greater than 500 units. The induction of many known IFN-regulated genes, such as Stat1, myxovirus resistance 1 (Mx-1), and ISGF-3, validated the approach. Using this list of IFN-regulated genes, 13 of 14 unique genes in the cluster were identified as bonafide IFN-regulated transcripts. Overall, 23 of the 161 genes (14.3%) were found to be IFN-regulated, compared with 7 genes (4.3%) that would have been expected by chance alone. The overrepresentation of interferon-regulated genes in the list of transcripts that best discriminated SLE patients from controls was consistently observed when a variety of different filters were used to define both IFN-regulated and SLE genes.

The mRNA levels of the IFNs themselves were not significantly different between patients and controls. Plasma/serum IFN-γ and IFN-α proteins were measured by ELISA (Pierce Endogen, Rockford, Ill.). IFN-γ was undetectable in all samples (less than 25 pg/mL). IFN-α was detectable in only two patients (26 and 29 pg/mL) and one control subject (56 pg/mL).

An IFN "score" was calculated for each patient and control, based on expression of genes in the IFN cluster. Scores were calculated by first normalizing the expression values within each row of genes so that the maximum value in any row was 1.0. Then the columns (samples) were summed to obtain the score. The IFN score (mean ±SD) for patients was 3.7±2.6, compared to controls 1.5±0.5, $p=4.2 \times 10^{-7}$. Approximately half of the SLE patients exhibited an elevated IFN score, while the others had scores indistinguishable from controls (FIG. 1).

The lupus patient population was divided into two groups, with the IFN-high group containing the 24 patients with the highest IFN scores, and the IFN-low group containing the 24 patients with the lowest scores. Differences in gene expression were examined. Table 4 contains a list of the genes that displayed differential expression between the IFN-high and IFN-low groups. All of the genes listed in Table 4 were expressed at a greater level in the IFN-high group that in the IFN-low group.

Figure 2:
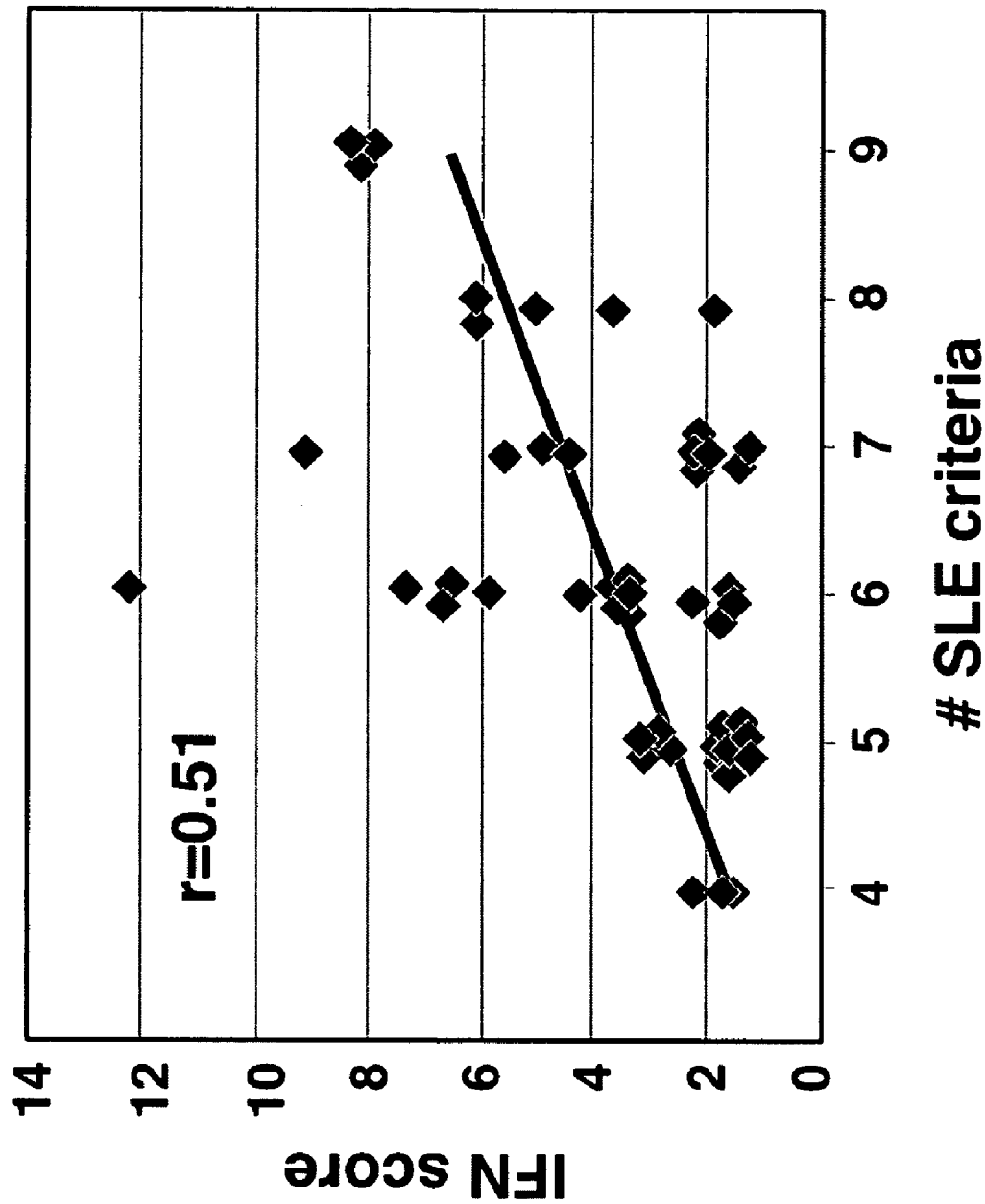
FIG. 2 is a graph plotting the number of SLE criteria observed in the 24 SLE patients with the highest IFN scores and in the 24 SLE patients with the lowest IFN scores; $p=0.002$.

Studies then were conducted to determine whether the IFN gene expression signature correlated with clinical features of SLE. SLE typically is diagnosed using eleven criteria developed by the ACR (Hochberg (1997) *Arthritis Rheum.* 40:1725). These criteria span the clinical spectrum of SLE and include skin criteria (malar rash, oral ulcers, photosensitivity, and discoid rash), systemic criteria (pleuritis or pericarditis, arthritis, renal disease, or CNS involvement), and laboratory criteria (cytopenias, anti-dsDNA or anti-phospholipid Abs, and antinuclear antibodies). A patient must meet four of these criteria to be classified as having definite SLE. The number of SLE criteria met by each patient was plotted against his or her IFN score (FIG. 2). This analysis revealed that the IFN score was correlated with the number of SLE criteria displayed in each patient.

Figure 3:
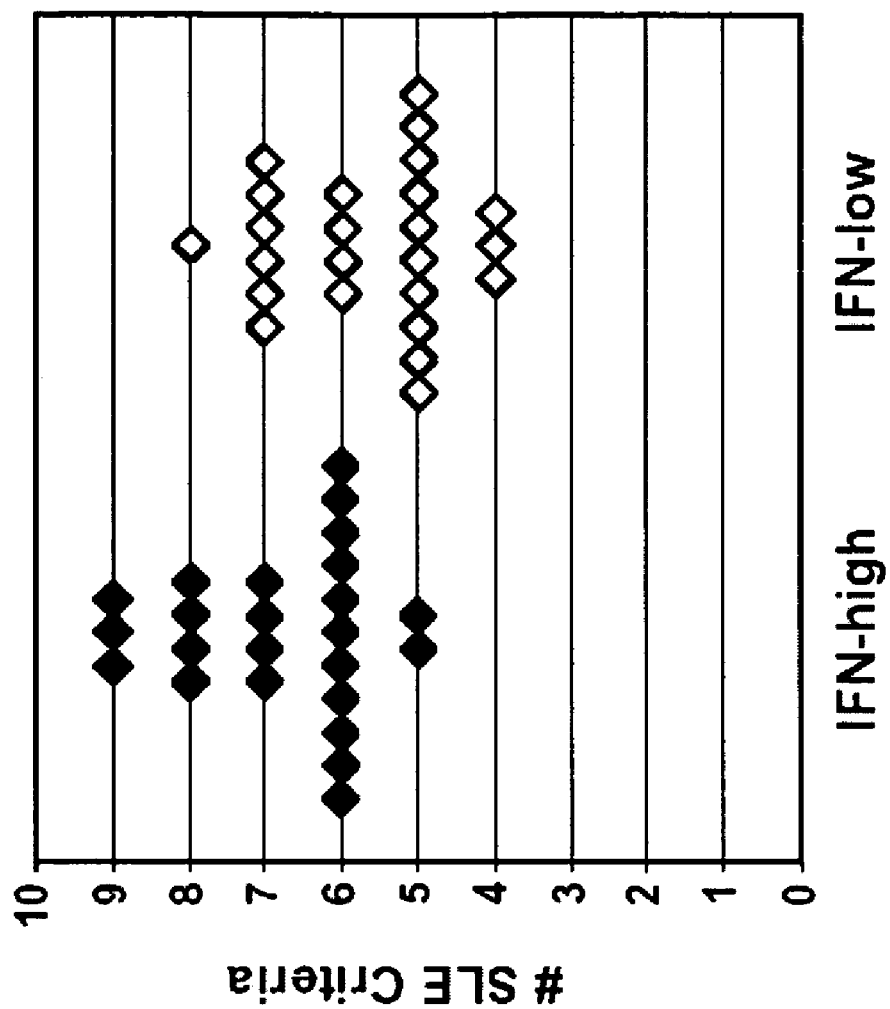
FIG. 3 is a graph plotting the number of SLE criteria met by each patient against the IFN score of each patient.
Figure 4:
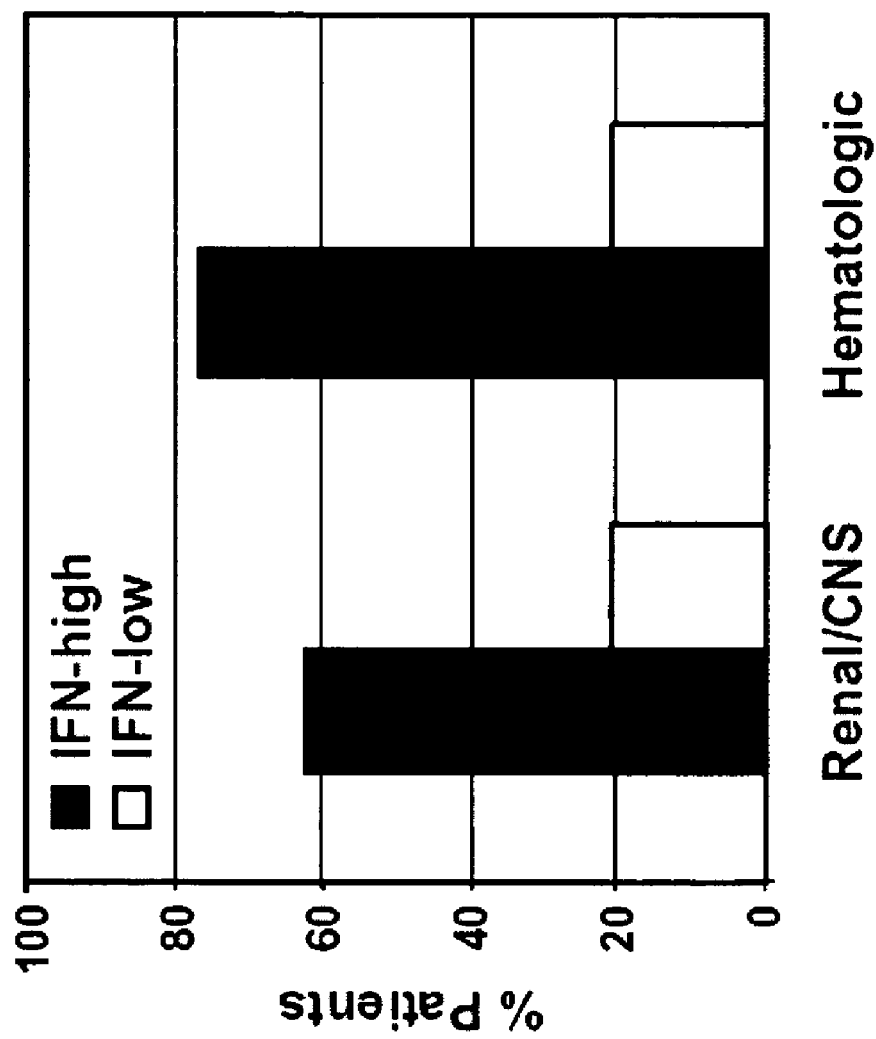
FIG. 4 is a bar graph showing the percent of patients in the IFN-high and IFN-low groups with ACR-defined criteria for renal and/or CNS disease ($p=7.7 \times 10^{-6}$) or hematologic involvement ($p=6.1 \times 10^{-9}$).

In a similar analysis, the clinical features of the 24 SLE patients with the highest IFN scores (IFN-high) were compared to the clinical features of the 24 SLE patients with the lowest scores (IFN-low). As depicted in FIG. 3, patients in the IFN-high group had a significantly higher number of SLE criteria (6.8±1.3) than those in the IFN-low group (5.7±1.1; p=0.004). Patients in the IFN-high group also showed a trend towards being diagnosed with SLE at an earlier age (25±12 compared with 30±13 years; p=0.192). Importantly, 15 of 24 patients (63%) in the IFN-high group fulfilled the ACR criteria for involvement of kidneys and/or the CNS, the most serious complications of lupus, compared with 5 of 24 patients (21%) in the IFN-low group (FIG. 4). In addition, 18 of 24 IFN-high patients (75%) showed hematologic involvement in their disease (severe leukopenia, hemolytic anemia or thrombocytopenia), compared with only 5 of 24 IFN-low patients (21%). An elevated interferon score thus correlated with the more severe manifestations of SLE.

The hypothesis that IFNs are important in the pathogenesis of lupus is supported by a number of observations. Mice transgenic for IFN-γ develop lupus-like autoimmunity (Seery et al. (1997) *J. Exp. Med.* 186:1451), and lupus-prone NZB/NZW F1 mice treated with anti-IFN-γ Abs or bred onto the IFN-γ$^{-/-}$ background show amelioration of disease (Jacob et al. (1987) *J. Exp. Med.* 166:798; and Balomenos et al. (1998) *J. Clin. Invest.* 101:364). The interferon-inducible gene IFI-202 has been identified as an SLE gene within the Nba2 SLE locus on mouse chromosome 1, NZB mice, the parental strain for this locus, show constitutively high expression of this transcription factor (Rozzo et al. (2001) *Immunity* 15:435). In humans, elevated levels of IFN-α have been reported in the sera of some SLE patients (for review see Ronnblom and Alm (2001) *J. Exp. Med.* 194:59), and a significant percentage of individuals treated with IFN-α for viral hepatitis develop lupus-related autoantibodies (Fukuyama et al. (2000) *Am. J. Gastroenterol.* 95:310). Finally, IFN-α in the sera of some pediatric SLE patients induces maturation of monocytes into highly active antigen-presenting plasmacytoid dendritic cells (Blanco et al. (2001) *Science* 294:1540).

While genes in IFN-signaling pathways exhibited dysregulated expression in some lupus patients, the mRNA levels of the IFNs themselves were not significantly different between patients and controls. IFN-γ protein was not detectable by ELISA in any patient or control sample, and IFN-α was detectable in only 2 of 48 patients and 1 of 42 controls. Thus, other cytokines that utilize Jak/Stat signaling pathways downstream of their receptors, such as IL-4, IL-13, or IL-2 (Hirano et al. (2000) *Oncogene* 19:2548), could contribute to the gene expression patterns observed.

Example 2

Identifying Additional Genes That Can Be Used to Diagnose SLE

Study participants: Patients were enrolled from the lupus clinic at Johns Hopkins University Medical Center (Petri et al. (1991) *Arthritis Rheum.* 34:937-944). All SLE patients had physician-verified SLE and were evaluated by the same examining physician. After informed consent, patients provided a peripheral blood sample. Blood for RNA extraction was collected into PaxGene tubes (PreAnalytiX, Hombrechtikon, Switzerland).

Sample Processing and Chip Hybridization: RNA was extracted using the PaxGene Blood RNA System (PreAnalytix). Five μg of total RNA was used to prepare biotinylated cRNA for hybridization using the standard Affymetrix protocol (Expression Analysis Technical Manual, Affymetrix, Santa Clara, Calif.). For seven samples with low RNA yields, two rounds of amplification were performed. Fifteen micrograms of each labeled cRNA was hybridized to Affymetrix U133A Human GeneChips.

Data Processing: Affymetrix Microarray Suite (MAS) 5.0 software was used to generate expression ("signal") values for each gene. To correct for slight differences in overall chip hybridization intensity and allow for comparison between samples, each chip was scaled to an overall intensity of 1500.

Comparison Analyses and Hierarchical Clustering: For selection of genes that were differentially expressed between the 81 SLE patients and 41 controls, the following three criteria were used: (i) $p<1 \times 10^{-5}$ by unpaired Student's t test, (ii) change in expression of at least 1.5-fold when comparing the means of the two groups, and (iii) difference in expression of at least 100 signal units when comparing the means of the two groups. A set of 405 genes met all three of these criteria and were selected for further analysis.

Hierarchical clustering was performed with CLUSTER and visualized with TREEVIEW (Eisen et al. (1998) *Proc. Natl. Acad. Sci. USA* 95:14863-14868). Prior to clustering, each data point for a given gene was divided by the mean expression value of the controls for that gene. The $\log_2$ of these ratios was then used as input for CLUSTER. Data were transformed in the same manner for k-means clustering using the same software package.

Calculation of Gene Expression Signature Scores: For calculation of signature scores, the expression values within each gene row were normalized so that the maximum value in any row was 1.0. For each sample, the normalized values for each gene in the signature were then summed to obtain the score. These scores were used to correlate gene expression signatures with clinical features. P-values for these correlations were generated by linear regression analysis. Signature scores also were used to calculate correlation coefficients between the various signatures in order to assess their interdependence.

Cell Sorting for Expression Profiling of purified Cell Subsets: For isolation of T cells, NK cells, monocytes, and neutrophils, blood was collected from healthy donors into ACD tubes (Becton-Dickinson, Franklin Lakes, N.J.). Total WBCs were separated from RBCs using Lympholyte-Poly (Cedarlane Labs, Homby, Ontario) according to the manufacturer's protocol. Any remaining RBCs were removed with RBC lysis buffer (Roche Applied Science, Basel, Switzerland). After blocking with 10% human serum, cells were stained for 15 minutes at 4° C. with CD3-APC, CD66B-FITC, CD64-CyC, and CD56-PE, and then washed with cold PBS+2% fetal bovine serum. A four-color, four-way sort was performed with the FacsVantage SE Turbo with FACS Diva option (BD Biosciences, San Jose, Calif.). Purity of populations was >90%. B cells were isolated following leukopheresis of control donors using a Miltenyi system for positive selection of CD19+ cells. RNA was isolated from the purified cell types using the RNeasy kit (Qiagen, Valencia, Calif.) and prepared for hybridization as described above.

Functional classes represented among differentially expressed genes: Blood samples were collected from 81 patients and from 41 healthy controls. Total RNA was isolated from WBCs and used to generate cRNA probes for hybridization to Affymetrix U133A GeneChips. The expression levels of 22,283 probe sets (representing 18,400 transcripts and variants) were compared between SLE patients and normal controls. 470 probe sets were identified (representing 405 transcripts) that met all three of the following criteria for differential expression: (i) $p<1\times10^{-5}$ by unpaired students t test, (ii) at least a 1.5-fold change between the SLE mean and control mean, and (iii) a difference of at least 100 signal units between the SLE mean and control mean.

To visualize the differences in gene expression between patients and controls, the data were transformed for each gene by dividing each signal value by the mean signal of the controls. Hierarchical clustering was then performed using the $\log_2$ of this ratio. The majority of patients were clustered together in this analysis, with the exception of two patients that clustered with the controls. There also were four controls that clustered in the SLE group. The enrichment of IFN-regulated genes, as identified by a previously described in vitro stimulation of normal PBMCs with IFN (Baechler et al. (2003) *Proc. Natl. Acad. Sci. USA* 100:2610-2615), was immediately apparent (90 genes). In particular, there was a tight cluster of 82 genes, 69 of which were induced by IFN in the in vitro experiment. This set of 82 genes was identified as the IFN signature, and this expression pattern was observed in ~75% of the patients. The majority of the IFN-regulated genes in this cluster were up-regulated by type I IFN (67 of 69 genes, average fold change greater than 2 in four in vitro experiments); and, many also were induced by type II IFN (IFN-γ, 48 of 69 genes with fold change greater than 2). The level of induction of these genes, measured by fold change relative to PBS control, generally was greater in response to IFN-α/β as compared to IFN-γ. Seventy of the genes comprising the IFN signature are listed in Table 5. In addition to the genes listed in Table 5, the IFN signature included the following: XIAP associated factor-1, LY6E, phospholipid scramblase 1, capicua homolog, 2'-5'-OAS-like, hypothetical (osteoblast), IFN-stimulated ptn 15 kDa, C1 inhibitor, IFN-alpha inducible (IFI-6-16), CD64, galectin 3 (lectin, galactosidase-binding, soluble 3 binding protein), and MX1 (myxovirus resistance 1). Twenty-one other IFN-regulated genes were not included in the IFN signature because their expression was not correlated with SLE activity. These are listed in Table 6.

TABLE 5

IFN signature

| Accession Number | Gene |
|---|---|
| AA740186 | biliverdin reductase A |
| NM_003113 | SP100 |
| NM_006442 | DR-associated ptn 1 |
| U03891 | APOBEC3A (phorbolin 1) |
| NM_004335 | BST-2 |
| NM_030776 | Z-DNA binding protein 1 |
| D43949 | hypothetical KIAA0082 |
| NM_005502 | ATP-binding cassette A1 |
| AW474434 | AW474434 |
| NM_018295 | FLJ11000 |
| NM_015675 | GADD45B |
| NM_001712 | biliary glycoprotein |
| NM_002450 | metallothionein 1L |
| M10943 | metallothionein 1F |
| NM_000593 | ATP-binding cassette B |
| AW188198 | TNF-alpha induced protein 6 |
| BC002666 | guanylate binding protein 1 |
| AF317129 | torsin B |
| NM_004223 | UBE2L6 |
| NM_016381 | 3' repair exonuclease 1 |
| NM_003641 | IFIT-1 (9-27) |
| BF338947 | IFIT-3 |
| AL121994 | hypothetical AL121994 |
| NM_005953 | metallothionein 2A |
| NM_005952 | metallothionein 1X |
| NM_023068 | sialoadhesin |
| NM_017414 | ubiquitin specific protease 18 |
| NM_017631 | hypothetical FLJ20035 |
| NM_005532 | IFN-alpha inducible 27 |
| NM_006187 | 2'-5'-OAS 3 |
| AK002064 | DNA polymerase-transactivated protein 6 (DKFZP564A2416 protein) |
| AA083478 | tripartite motif-containing 22 |
| NM_016816 | 2',5'-OAS 1 |
| NM_004030 | IFN regulatory factor 7 |
| NM_001549 | IFIT-4 |
| BE049439 | IFN-induced protein 44 |
| NM_001548 | IFIT-1 |
| NM_016323 | cyclin-E binding protein 1 |
| NM_022750 | poly (ADP-ribose) polymerase family, member 12 (hypothetical FLJ22693) |
| NM_016817 | 2'-5'-OAS 2 |
| NM_022147 | 28 kD IFN responsive protein |
| N47725 | retinoic acid and IFN-inducible |
| NM_015907 | leucine aminopeptidase |
| BC001356 | IFN-induced protein 35 |
| NM_017912 | hect domain and RLD 6 (hypothetical protein FLJ20637) |
| NM_002463 | MX2 |
| NM_005138 | SCO2 |
| U65590 | IL-1 receptor antagonist |
| AI719655 | caspase 1 |
| U57059 | TNF SF10 |
| NM_004688 | N-myc (and STAT) interactor |
| NM_006519 | t-complex-associated 1-like 1 |
| NM_002970 | N1-acetyltransferase |
| NM_005531 | IFN-gamma inducible 16 |
| BF055474 | NY-REN-34 antigen |
| NM_002201 | IFN stimulated gene (20 kD) |
| NM_007315 | STAT1 |
| NM_022168 | IFI-H1 |
| NM_014314 | RNA helicase |
| AI421071 | CCR1 |
| AL031602 | IBR domain containing 3 (hypothetical AL031602) |

TABLE 5-continued

IFN signature

| Accession Number | Gene |
|---|---|
| BF217861 | metallothionein 1E |
| NM_005951 | metallothionein 1H |
| NM_017654 | sterile alpha motif domain containing 9 (hypothetical FLJ20073) |
| NM_002675 | promyelocytic leukemia |
| NM_014398 | LAMP3 |
| NM_014628 | MAD2L1 binding protein (hypothetical NM_14628) |
| NM_005771 | retinol dehydrogenase homolog |
| NM_024021 | membrane-spanning 4-domains, subfamily A, member 4 (CD20) |
| AI337069 | radical S-adenosyl methionine domain containing 2 (AI337069) |

TABLE 6

IFN-regulated genes not included in the IFN signature

| Accession No. | Gene |
|---|---|
| BC005907 | histamine N-methyltransferase (BC005907) |
| NM_015961 | Chromatin modifying protein 5 (NM_015961) |
| NM_001803 | CDW52 antigen (CAMPATH-1 antigen) |
| BF590263 | chondroitin sulfate proteoglycan 2 (versican) |
| NM_005213 | cystatin A (stefin A) |
| U08092 | histamine N-methyltransferase |
| NM_000416 | interferon gamma receptor 1 |
| BG540628 | immunoglobulin kappa constant |
| NM_001565 | small inducible cytokine subfamily B (Cys-X-Cys), member 10 |
| NM_002759 | protein kinase, interferon-inducible double stranded RNA dependent |
| NM_002818 | proteasome (prosome, macropain) activator subunit 2 (PA28 beta) |
| NM_021136 | reticulon 1 |
| NM_005621 | S100 calcium binding protein A12 (calgranulin C) |
| AI056051 | JAK binding protein |
| BE962483 | tripartite motif-containing 14 |
| NM_014857 | RAB GTPase activating protein 1-like (KIAA0471 gene product) |
| NM_006406 | peroxiredoxin 4 |
| AV699744 | KIAA0650 protein |
| AI082078 | translocase of inner mitochondrial membrane 10 homolog (yeast) |
| NM_016184 | C-type (calcium dependent, carbohydrate-recognition domain) lectin, superfamily member 6 |
| NM_016619 | placenta-specific 8 (hypothetical protein) |

In addition to the IFN signature, several other functionally interesting gene groups were identified among the transcripts differentially expressed in SLE. There were 29 genes encoding ribosomal protein subunits among the 405 differentially expressed genes. One particularly tight cluster was specifically enriched for ribosomal transcripts (14 of 15 transcripts). There also were 35 transcripts encoding mitochondrial proteins that were over-expressed in the lupus samples. Interestingly, the expression patterns of the ribosomal genes and the mitochondrial genes were highly similar across the lupus patients. In order to assess the degree of similarity between these two signatures, a ribosomal score was calculated using the 15-gene cluster, and a mitochondrial score was calculated using the 35 mitochondrial genes. These scores were very highly correlated (r=0.87), indicating that the two signatures can be considered as one (Table 7).

TABLE 7

Ribosomal/mitochondrial signature

| Accession No. | Gene |
|---|---|
| *Ribosomal* | |
| L05095 | RPL30 |
| BE968801 | RPL35A |
| NM_001032 | RPS29 |
| N32864 | HINT1 |
| AA320764 | RPS10 |
| NM_000988 | RPL27 |
| NM_001019 | RPS15a |
| BC001019 | RPL39 |
| NM_000971 | RPL7 |
| NM_001006 | RPS3A |
| AI348010 | RPL31 |
| NM_000661 | RPL9 |
| NM_001021 | RPS17 |
| AI805587 | RPS7 |
| *Mitochondrial* | |
| NM_014180 | mito. ribosomal protein L22 |
| NM_016055 | mito. ribosomal protein L48 |
| NM_014018 | mito. ribosomal protein S28 |
| BE782148 | mito. ribosomal protein L42 |
| BC003375 | mito. ribosomal protein L3 |
| NM_006636 | MTHFD2 |
| NM_004889 | ATP5J2 |
| NM_004373 | COX6A1 |
| NM_001866 | COX7B |
| NM_006830 | UQCR |
| NM_006886 | ATP5E |
| NM_001685 | ATP5J |
| NM_014402 | QP-C |
| NM_020548 | diazepam binding inhibitor |
| NM_004374 | COX6C |
| NM_001867 | COX7C |
| NM_004894 | chr 14 ORF 2 |
| NM_006476 | ATP5L |
| NM_001865 | COX7A2 |
| NM_005174 | ATP5C1 |
| NM_004546 | NADH dehyd. (ubiquinone) 1 beta 2 |
| NM_002489 | NADH dehyd. (ubiquinone) 1 alpha 4 |
| NM_006004 | UQCRH |
| NM_001697 | ATP5O |
| NM_016071 | mito. ribosomal protein S33 |
| BC002772 | NADH dehyd. (ubiquinone) 1 alpha 6 |
| NM_002491 | NADH dehyd. (ubiquinone) 1 beta 3 |
| AF313911 | thioredoxin |
| NM_006406 | peroxiredoxin 4 |
| NM_004545 | NADH dehyd. (ubiquinone) 1 beta 1 |
| NM_016622 | mito. ribosomal protein L35 |
| NM_020139 | oxidoreductase UCPA |
| NM_012459 | TIMM8B |
| NM_006327 | TIMM23 |

Three additional genes encoding mitochondrial proteins were expressed at lower levels in SLE. Also among the genes down-regulated in SLE was a tight cluster of genes that exhibited a more dramatic decrease in expression in a subset of samples (30 transcripts). Many of these genes encode proteins related to transcription or other nuclear processes, including the transcriptional regulators retinoblastoma-like 2 (RBL2), F-box and leucine-rich repeat protein 11 (FBXL11), and nuclear receptor subfamily 1, group D, member 2 (NR1D2), as well as other nucleic acid binding proteins such as chromodomain helicase DNA binding protein 4 (CHD4), KH domain containing, RNA binding, signal transduction associated 1 (KHDRBS1), serine/arginine repetitive matrix 2 (SRRM2), and RAD21. These are listed in Table 8.

TABLE 8

Nuclear/transcription signature

| Accession No. | Gene |
| --- | --- |
| N32859 | NR1D2 |
| NM_004486 | golgi autoantigen A2 |
| AI761771 | CHD4 |
| BG289967 | RAD21 homolog |
| X76061 | retinoblastoma-like 2 |
| NM_014857 | RAB GTPase activating protein 1-like (KIAA0471) |
| NM_006559 | KHDRBS1 |
| BE538424 | BE538424 |
| Y09216 | DYRK2 |
| AK001699 | F-box only protein 21 |
| NM_003316 | TTC3 |
| NM_002185 | IL7R |
| AI557319 | AI557319 |
| AW149364 | SFRS protein kinase 2 |
| NM_004719 | SFRS2IP |
| NM_016333 | SRRM2 |
| NM_012201 | Golgi apparatus protein 1 |
| NM_000565 | IL6R |
| NM_002385 | myelin basic protein |
| NM_005892 | formin-like |
| U48734 | actinin, alpha 4 |
| AW237172 | Jumonji domain containing 2B (KIAA0876 protein) |
| NM_007371 | bromodomain-containing 3 |
| AI356398 | zinc finger protein 36 |
| AK022014 | A kinase (PRKA) anchor protein 13 (hypothetical protein FLJ11952) |
| AK024505 | f-box and leucine-rich repeat 11 |
| AI830698 | IGF1R |
| AI741124 | G protein, beta 1 |
| BF246499 | Tyrosine 3-monooxygenase/tryptophan 5-monooxygenase activation protein, beta polypeptide (GW128 protein) |
| NM_018340 | hypothetical protein FLJ11151 |

Another notable group of genes included a set of 28 transcripts whose expression was correlated with the percentage and absolute number of neutrophils in the patients' blood samples. In order to determine if these genes were specifically expressed in neutrophils, microarray analysis was performed on purified populations of T cells, B cells, NK cells, monocytes, and neutrophils from normal donors. Of these 28 genes, 13 were highly expressed in neutrophils as compared to other WBC subsets (fold change of at least 10 when compared to at least one other cell type; Table 9). Several of these genes were also highly expressed in monocytes, but the expression of these genes in the patient population did not correlate with the percentage or number of monocytes in the patients' blood samples.

TABLE 9

Neutrophil signature

| Accession No. | Gene |
| --- | --- |
| NM_004666 | vanin 1 |
| NM_003853 | IL18R accessory protein |
| AF153820 | KCNJ2 |
| NM_004334 | BST1 |
| AL353759 | histone 1, H2ac (H1 histone family, member 4) |
| NM_004049 | BCL2-related protein A1 |
| M63310 | annexin A3 |
| AB014550 | KIAA0650 protein |
| NM_004125 | G protein, gamma 10 |
| NM_015364 | lymphocyte antigen 96 (MD-2 protein) |
| NM_002964 | S100 calcium binding ptn A8 |

TABLE 9-continued

Neutrophil signature

| Accession No. | Gene |
| --- | --- |
| NM_005621 | S100 calcium binding ptn A12 |
| NM_005213 | cystatin A |

Patterns of heterogeneity in lupus blood: The expression patterns of the gene groups suggest that, in addition to contributing to the distinction between SLE patients and normal controls, these signatures reflect a significant degree of heterogeneity within the patient population. As an unsupervised method of identifying patient subgroups, the patient samples were subjected to k-means clustering. As input for the clustering, $\log_2$-transformed expression ratios (sample signal divided by control mean signal) were used for 151 genes (82 IFN signature genes, 15 ribosomal signature genes, 11 mitochondrial signature genes, 13 neutrophil signature genes, and 30 nuclear/transcription signature genes). Following k-means analysis (k=4), one-dimensional hierarchical clustering of the same 151 genes was performed with the sample order fixed according to the subgroups defined by k-means clustering. The k-means algorithm identified the following four subsets of SLE patients: (i) nuclear/transcription positive, ribosomal/mitochondrial positive, IFN positive (n=11); (ii) mitochondrial/ribosomal positive, IFN negative (n=21); (iii) mitochondrial/ribosomal negative, IFN positive (n=25); (iv) ribosomal/mitochondrial positive, IFN positive (n=24).

The IFN signature correlates with disease severity and immunologic abnormalities: In order to assess the potential association of these gene expression signatures with clinical manifestations of SLE, correlation coefficients were calculated between the signature scores and clinical features. The significance of the correlations was determined by linear regression analysis. In order to visualize the correlations in the context of the clustering result, correlation coefficients also were calculated between the expression of each individual gene and the clinical features, and correlation curves were plotted as moving windows (11-gene average).

The IFN signature was highly correlated with disease activity as measured by the SLE disease activity index (SLE-DAI; Table 10). The correlation between the IFN score and SLEDAI was highly significant (r=0.38, p=3.9×10$^{-4}$ by linear regression). Several laboratory measures often associated with disease activity, such as leukopenia and elevated erythrocyte sedimentation rate (ESR), also were correlated with the IFN signature (ESR, r=0.38, p=5.4×10$^{-4}$; WBC, r=−0.38, p=4.7×10$^{-4}$). Body weight was significantly decreased in IFN-high patients (r=−0.46, p=1.7×10$^{-5}$). Patients with high IFN scores were more likely to have required cytotoxic therapy at some point in their disease course (r=0.27, p=0.02), although they were not more likely to be receiving immunosuppressive therapy at the time of blood draw (r=0.07, p=0.56). Perhaps as the ultimate measure of historical disease activity, a number of patients in the study have required hospitalization at some point because of their lupus (n=40). The number of hospitalizations per patient ranged from 1 to 10 (mean=2.9, SD=2.5). The number of SLE hospitalizations was positively correlated with the IFN score (r=0.31, p=0.009). A smaller number of patients required hospitalization for infectious complications (n=17); this was slightly, though non-significantly, correlated with IFN score (r=0.23, p=0.06). These data support the conclusion that the IFN signature is a marker for severe and active SLE.

Another striking result of this analysis is the strong evidence linking the IFN signature with immunologic abnormalities, both current and historical. The IFN signature exhibited strong negative correlation with current visit C3 and C4 levels (C3, $r=-0.47$, $p=1.0\times10^{-5}$; C4, $r=-0.37$, $p=6.4\times10^{-4}$). Accordingly, IFN scores were higher in the subset of patients fulfilling the SLEDAI component for low complement (n=30, IFN score 32.8±10.7) than in patients who did not fulfill this component (n=51, IFN score 23.5±11.4, $p=4\times10^{-4}$). The IFN score was also correlated with a history of low complements (low C3, $r=0.51$, $p=4.0\times10^{-6}$; low C4, $r=0.34$, $p=0.003$).

The autoantibody profiles of these SLE patients also correlated with the expression of the IFN signature genes. Both current visit and historical presence of antibodies against dsDNA correlated positively with the IFN score (current anti-DNA titer, $r=0.37$, $p=6.2\times10^{-4}$; historical anti-DNA, $r=0.53$, $p=1.1\times10^{-6}$). The historical presence of antibodies against RNA binding proteins exhibited a trend towards correlation with IFN scores, although not statistically significant in all cases (anti-Ro, $r=0.30$, $p=0.01$; anti-La, $r=0.23$, $p=0.05$; anti-RNP, $r=0.21$, $p=0.07$). Despite the non-significant p-value of the anti-RNP correlation, the IFN scores of patients who at some point tested positive for anti-RNP (n=23, IFN score 30.4±7.1) were significantly higher than those of patients who have never tested positive for anti-RNP (n=49, IFN score 25.4±12.2, $p=0.03$). Finally, the presence of anti-erythrocyte antibodies was correlated with IFN score (Coombs test, $r=0.29$, $p=0.04$). This finding is consistent with the observation that patients with elevated IFN scores were more likely to have experienced anemia during their disease course ($r=0.26$, $p=0.03$). Taken together, these data show that immunological abnormalities are a prominent feature of lupus patients that exhibit the IFN signature.

TABLE 10

Correlation of IFN signature with clinical features

| Clinical Feature | r-value with IFN score | p-value | Clin+ vs. Clin− | Correlation curve |
|---|---|---|---|---|
| Current ||||
| SLEDAI | 0.38 | 3.9E−04 | 0.002 | p < 0.005 |
| Low C' | 0.38 | 5.1E−04 | 4.2E−04 | p < 0.001 |
| Inc. anti-DNA | 0.38 | 4.8E−04 | 4.4E−04 | p < 0.0005 |
| ESR | 0.38 | 5.4E−04 | | p < 0.001 |
| RDW | 0.29 | 0.023 | | p < 0.05 |
| C3 | −0.47 | 1.0E−05 | | p < 0.0001 |
| C4 | −0.37 | 6.4E−04 | | p < 0.005 |
| anti-DNA titer | 0.37 | 6.2E−04 | 6.7E−04 | p < 0.005 |
| HCT | −0.32 | 0.002 | | p < 0.0005 |
| HGB | −0.33 | 0.007 | | p < 0.005 |
| WBC | −0.38 | 4.7E−04 | | p < 0.005 |
| Lymph # | −0.42 | 8.8E−04 | | p < 0.005 |
| Lymph % | −0.29 | 0.024 | | p < 0.01 |
| Neutro % | 0.27 | 0.032 | | p < 0.01 |
| Weight | −0.46 | 1.7E−05 | | p < 0.0005 |
| BP diastolic | −0.24 | 0.034 | | p < 0.05 |
| BP systolic | −0.28 | 0.013 | | p < 0.05 |
| Historical ||||
| #SLE hosp. | 0.31 | 0.009 | 0.002 | p < 0.05 |
| # Infect. hosp. | 0.23 | 0.055 | 0.046 | p < 0.05 |
| Low C3 | 0.51 | 4.0E−06 | 1.6E−06 | p < 0.0001 |
| Low C4 | 0.34 | 0.003 | 0.002 | p < 0.005 |
| Anti-DNA | 0.53 | 1.1E−06 | 3.6E−08 | p < 0.0005 |
| Anti-Ro | 0.30 | 0.011 | 0.012 | p < 0.05 |
| Anti-La | 0.23 | 0.049 | 0.062 | ns |
| Anti-RNP | 0.21 | 0.073 | 0.032 | ns |
| Coombs | 0.298 | 0.044 | 0.019 | p < 0.05 |
| Anemia | 0.26 | 0.028 | 0.027 | p < 0.05 |
| Cytotoxic | 0.27 | 0.022 | 0.017 | p < 0.05 |

TABLE 11

Correlation of ribosomal/mitochondrial signature with clinical features

| Clinical Feature | r-value with IFN score | p-value | Clin+ vs. Clin− | Correlation curve |
|---|---|---|---|---|
| Current ||||
| Inc. anti-DNA | −0.29 | 0.009 | 0.007 | p < 0.005 |
| Neutro % | −0.27 | 0.033 | | p < 0.05 |
| Historical ||||
| Photosensitivity | −0.25 | 0.029 | 0.027 | p < 0.05 |
| NSAIDs | 0.27 | 0.021 | 0.022 | p < 0.05 |

TABLE 12

Correlation of neutrophil signature with clinical features

| Clinical Feature | r-value with IFN score | p-value | Clin+ vs. Clin− | Correlation curve |
|---|---|---|---|---|
| Current ||||
| Pred. dose | 0.133 | 0.003 | | p < 0.05 |
| WBC | 0.29 | 0.010 | | p < 0.05 |
| Neutro % | 0.54 | 7.9E−06 | | p < 0.0005 |
| Neutro # | 0.37 | 0.003 | | p < 0.05 |
| Lymph % | −0.55 | 5.2E−06 | | p < 0.0005 |
| Mono % | −0.40 | 1.4E−03 | | p < 0.005 |
| Historical ||||
| Raynaud's | 0.35 | 0.003 | 0.002 | p < 0.01 |
| Lupus anticoag | 0.61 | 0.007 | 0.040 | p < 0.05 |
| Thrombocytopenia | 0.32 | 0.005 | 0.020 | p < 0.05 |
| NSAIDs | 0.24 | 0.040 | 0.025 | p < 0.05 |

TABLE 13

Correlation of nuclear/transcription signature with clinical features

| Clinical Feature | r-value with IFN score | p-value | Clin+ vs. Clin− | Correlation curve |
|---|---|---|---|---|
| Current ||||
| Neutro # | 0.28 | 0.031 | | p < 0.005 |
| Historical ||||
| Anti-RNP | −0.24 | 0.046 | 0.054 | ns |
| Anti-DNA | −0.24 | 0.038 | 0.042 | p < 0.05 |
| Anti-SM | −0.24 | 0.038 | 0.050 | ns |
| Anemia | −0.28 | 0.016 | 0.016 | p < 0.05 |
| Proteinuria | −0.36 | 0.002 | 0.002 | p < 0.01 |
| Hematuria | −0.23 | 0.054 | 0.085 | ns |

Tables 10-13 list clinical features significantly correlated with gene expression signatures. Clinical manifestations present either at the time of blood draw (Current) or at some point in the patient's history (Historical) were correlated with the indicated gene expression signatures. Correlations are presented as r-values, with p-values derived from linear regression. For clinical features where the patient is either positive or negative for the feature (e.g., Anti-DNA antibodies), signature scores of patients positive for the feature (Clin+) were compared to the scores of patients negative for the feature (Clin−). The p-values from unpaired t-test of these two groups are presented in the "Clin+ vs. Clin−" columns. For SLEDAI, the comparison was between patients with SLEDAI≦1 and patients with SLEDAI≧6. Random permutation analysis was used to generate p-values. ns, not significant ($p>0.05$); C', complement; Inc., increased.

Ribosomal/mitochondrial signature: Fifteen genes encoding ribosomal protein subunits, together with HINT 1, a histidine triad nucleotide binding protein whose physiological function is unknown, formed a tight cluster in the hierarchical clustering of all 405 SLE genes. A group of 35 genes encoding mitochondrial proteins displayed an expression pattern remarkably similar to the ribosomal pattern. Indeed, the ribosomal signature score and the mitochondrial score were highly correlated (r=0.87). Since the mitochondrial genes included a number of cytochrome C oxidase subunits (5 of 35 mitochondrial genes) as well as several subunits of the $F_1F_0$ ATP synthase (6 of 35 genes), experiments were conducted to examine the ability of 11 classical mitochondrial genes to substitute for the entire set of 35 mitochondrial genes observed in the SLE dataset. The signature consisting of the 11 classical genes was nearly identical to the full mitochondrial signature (r=0.98) and remained highly correlated with the ribosomal signature (r=0.89). Given this striking degree of similarity, the 11 core mitochondrial genes and the 15 ribosomal cluster genes were considered as a single gene expression signature (the ribosomal/mitochondrial signature).

Although there were few clinical features significantly correlated with the ribosomal/mitochondrial signature, one notable finding was the negative association of this signature with antibodies against DNA (Table 11). The ribosomal/mitochondrial score was inversely correlated with fulfillment of the SLEDAI component for anti-DNA antibodies (r=−0.29, p=0.009). Although the score was not significantly correlated with the anti-DNA titer at the time of blood draw, patients that lacked anti-DNA antibodies (n=48, IFN score 9.3±4.4) had higher ribosomal/mitochondrial scores than patients that tested positive for anti-DNA (n=33, IFN score 7.1±4.0, p=0.02). This signature also exhibited a negative correlation with photosensitivity (r=−0.25, p=0.03) and with the percentage of neutrophils in the patients' blood samples (r=−0.27, p=0.03).

Neutrophil signature: Using the expression of the 13 neutrophil genes to calculate the neutrophil score, it was observed that expression of these genes correlated positively with the current dose of prednisone (Table 12; r=0.33, p=0.003). Prednisone leads to the de-margination of neutrophils from vascular endothelium, which may account for this association. Interestingly, the neutrophil signature was also significantly correlated with a history of Raynaud's phenomenon (r=0.35, p=0.003). Also, although not correlated with current visit platelet counts, the signature was correlated with a history of low platelets (r=0.32, p=0.005). Despite the small number of patients for which data was available for the presence of lupus anticoagulant (LAC; 18 patients had data available, 4 were positive for LAC), the correlation between the neutrophil score and LAC was high enough to achieve statistical significance (r=0.61, p=0.007). This result must be interpreted with caution due to the small sample size.

Nuclear/transcription signature: The primary distinguishing feature of the genes that were decreased in expression in SLE was a group of 30 genes that exhibited a more dramatic change in a subset of patients. Many of these genes are known to have functions related to transcription or other nuclear processes. Because the expression of these genes is decreased in SLE, the patients with a greater fold-decrease in expression are said to carry the nuclear/transcription signature.

Interestingly, the expression of these genes was negatively correlated with several lupus autoantibodies (Table 13). In particular, antibodies against some ribonucleoprotein components were found more frequently in the patients carrying the nuclear/transcription signature (i.e., those with lower expression of those genes). This was true for anti-Sm and anti-RNP (Sm r=−0.24, p=0.04; RNP r=−0.24, p=0.05) but not for anti-Ro or anti-La (Ro r=−0.01, p=0.92; La r=0.08, p=0.53). A positive anti-DNA test at some point during disease course was also inversely correlated with the nuclear/transcription score (r=−0.24, p=0.04). This expression signature also correlated negatively with a history of anemia (r=−0.28, p=0.02). Also considering the patient's history, a negative correlation was observed with two measures of kidney involvement (proteinuria r=−0.36, p=0.002; hematuria r=−0.23, p=0.05).

Patient subsets defined by presence or absence of multiple gene signatures: Although the signature score approach reveals interesting clinical correlations, it does not account for clinical features that might be dependent upon the combined presence or absence of more than one signature. In order to identify such features, the clinical profiles of the four lupus subsets identified were compared by k-means clustering of 151 SLE genes. Visualization of the clustering result revealed that these patient subsets are defined by the presence or absence of three signatures: IFN, ribosomal/mitochondrial, and nuclear/transcription. The signature combinations defining the four patient groups are as follows: Group 0, ribosomal/mitochondrial positive, IFN positive, nuclear/transcription positive (n=11); Group 1, ribosomal/mitochondrial positive, IFN negative, nuclear/transcription negative (n=21); Group 2, ribosomal/mitochondrial negative, IFN positive, nuclear/transcription negative (n=25); and Group 3, ribosomal/mitochondrial positive, IFN positive, nuclear/transcription negative (n=24). The significance of an association between a clinical feature and a particular subgroup was estimated by comparing the patients belonging to that subgroup against all other patients using a chi-squared test for binary clinical variables and an unpaired t-test for continuous variables.

Figure 5A:
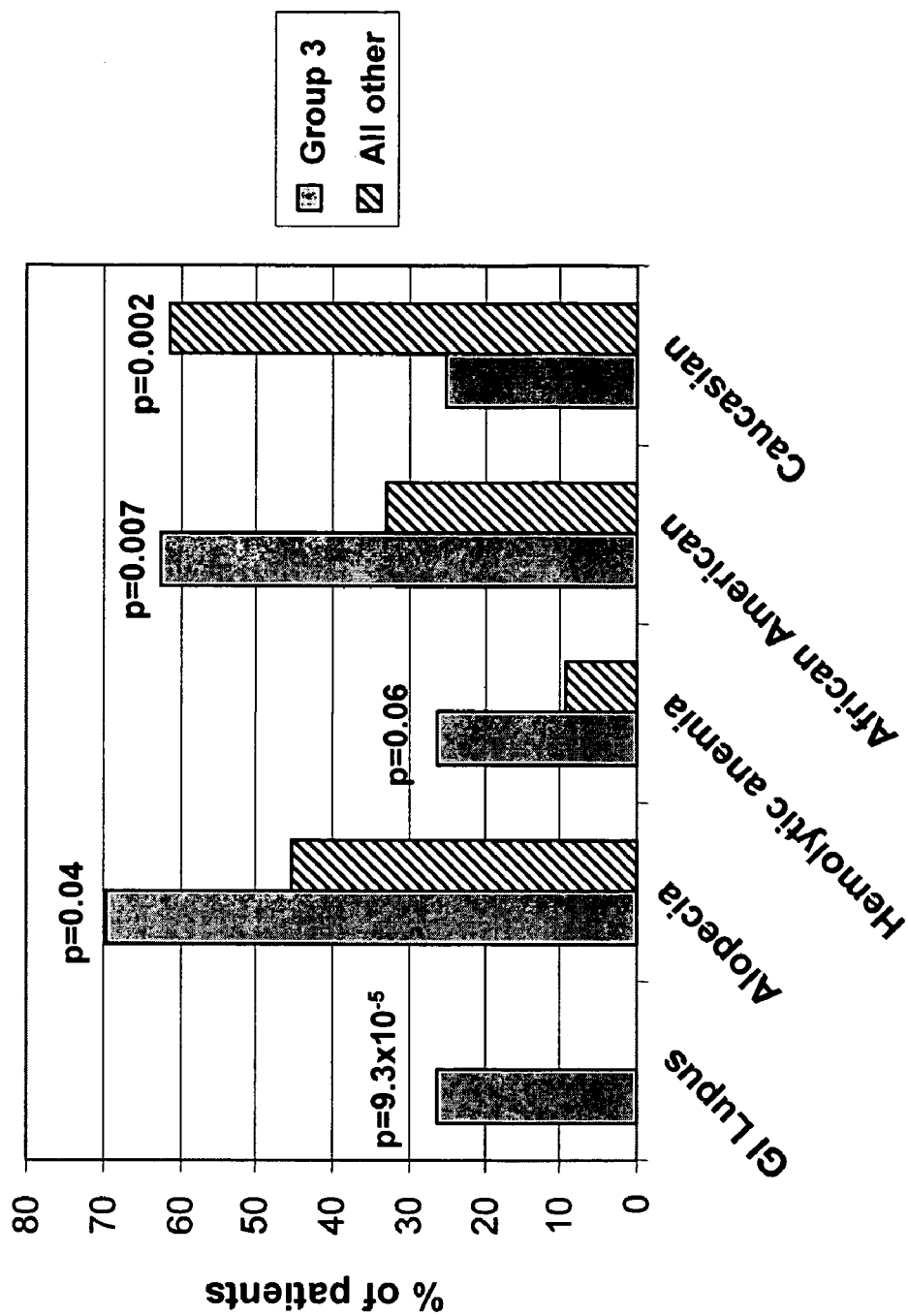
FIGS. 5A and 5B are graphs showing the percentage of SLE patients that exhibit particular clinical features, correlated with patient subgroup.

A number of clinical features were associated with patient group 3 (positive for both ribosomal/mitochondrial and IFN signatures but negative for nuclear/transcription signature, FIG. 5A). Among the 81 patients enrolled in this study, the only incidence of gastrointestinal lupus occurred in group 3 (6 of 23 patients, or 26%, p=9.3×10$^{-5}$). The frequency of alopecia was also significantly higher in group 3 than in the other groups combined (16/23 or 70% of group 3 vs. 24/54 or 44% of all other patients, p=0.04). Although not significant, there was a slight enrichment of patients with a history of hemolytic anemia in group 3 (6/23 or 26% of group 3 vs. 5/53 or 9% of all others, p=0.06). While the other patient groups consisted of between 55% and 67% Caucasians, only 25% of the patients in group 3 were Caucasian (p=0.002). This difference was primarily accounted for by an increased frequency of African American patients (63% of group 3 vs. 27% of all others, p=0.007).

Figure 5B:
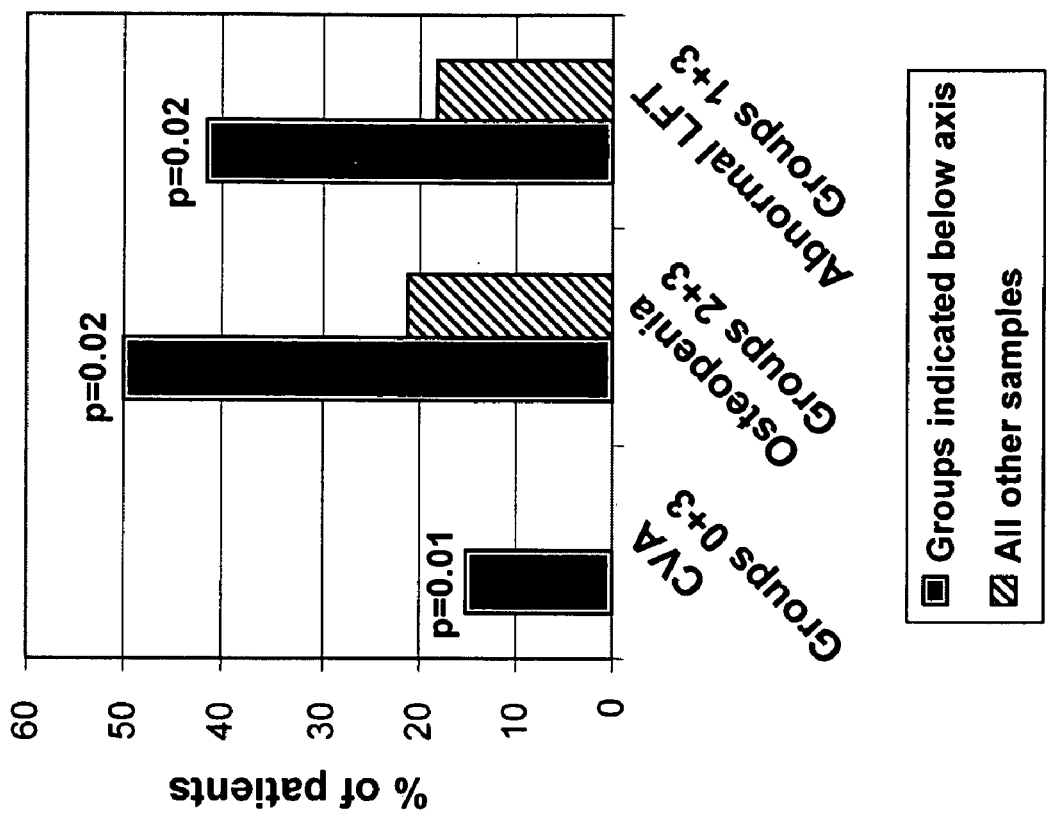

In addition to considering single patient subgroups, pairs of subgroups that were associated with particular clinical features also were considered as compared to the other two patient subgroups (FIG. 5B). Although the frequency of cerebrovascular accident (CVA) in this SLE population was quite low, the only patients with this complication occurred in groups 0 and 3 who exhibited both the IFN and ribosomal/mitochondrial signatures with or without the nuclear/transcription signature (5/33 or 15% of patients in groups 0 and 3 vs. 0/40 other patients, p=0.01). History of osteopenia was more frequent in groups 2 and 3, whose patients were IFN positive but nuclear/transcription negative with or without the ribosomal/mitochondrial signature (20/40 or 50% of patients in groups 2 and 3 vs. 6/28 or 21% of all other patients, p=0.02). Finally, patients in groups 1 and 3 (ribosomal positive but nuclear/transcription negative with or without the IFN signature) were more likely to have had an abnormal liver function test (18/43 or 42% of group 1 and 3 vs. 6/34 or 18% of all other patients, p=0.02).

Figure 6A:
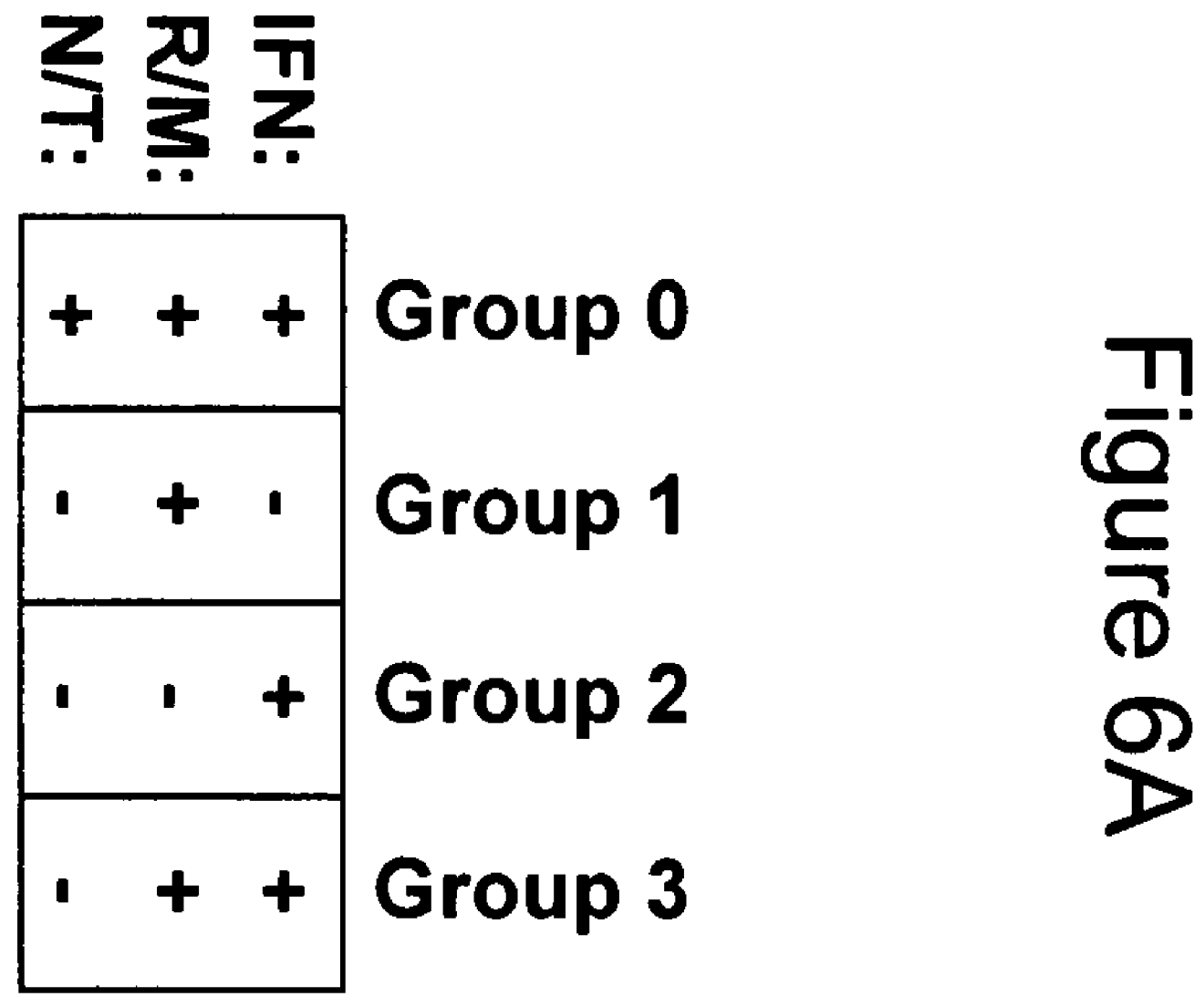

Heterogeneity within IFN signature positive patients: The set of clinical features associated with the IFN signature is described herein. K-means clustering of the lupus patient data revealed three subtypes of IFN signature positive patients (FIG. 6A): (i) those that also carry the ribosomal/mitochondrial signature with the nuclear/transcription signature (group 0), (ii) those that also carry the ribosomal/mitochondrial signature in the absence of the nuclear/transcription signature (group 3), and (iii) those that lack both the ribosomal/mitochondrial and nuclear/transcription signatures (group 2). Experiments were conducted to determine whether some features associated with the IFN signature might be specifically associated with one of these IFN positive subtypes.

A history of proteinuria was not associated with the IFN signature in this patient population (28/57 or 49% of IFN positive patients vs. 6/20 or 30% of IFN negative patients, p=0.14). This was surprising, since a correlation had previously been observed between renal involvement and the IFN signature. However, the frequency of proteinuria was significantly higher in the IFN positive subset that also exhibited both the ribosomal/mitochondrial and nuclear/transcription signatures (FIG. 6B; 8/11 or 73% of group 0 vs. 26/66 or 39% of all other patients, p=0.04).

While the SLEDAI components for low complements and increased anti-DNA antibodies were significantly associated with the IFN signature as a whole, the frequency of these immunologic abnormalities was found to be particularly high in the IFN positive patients that were negative for the ribosomal/mitochondrial signatures (FIG. 6C; low complement, 15/25 or 60% of group 2 vs. 16/56 or 29% of all other patients, p=0.007; anti-DNA, 18/25 or 72% of group 2 vs. 12/56 or 21% of all other patients, p=1.3×10$^{-5}$). In the case of anti-DNA antibodies, the p-value from the comparison of group 2 vs. all other patients was even more significant than the p-value from the comparison of all IFN positive patients vs. the IFN negative patients (p=3.7×10$^{-4}$). This is consistent with the observation that the ribosomal/mitochondrial signature is negatively correlated with the anti-DNA component of the SLEDAI.

Autoantibodies against the RNA-binding proteins Ro and La were also correlated with the IFN signature as a whole, although for anti-La the correlations did not reach statistical significance (Table 10). These autoantibodies were particularly associated with the IFN positive patients that were also positive for the ribosomal/mitochondrial signature but lacked the nuclear/transcription signature (FIG. 6D; anti-Ro, 13/23 or 57% of group 3 vs. 12/52 or 23% of all other patients, p=0.003; anti-La, 8/23 or 35% of group 3 vs. 4/52 or 8% of all other patients, p=0.005). Consideration of only the group 3 subset of IFN positive patients provided the statistical significance for anti-La that was lacking when the IFN signature was considered as a whole.

The requirement for cytotoxic therapy has been shown to be associated with the IFN signature (Table 10). However, the frequency of patients in the IFN positive group having received cytotoxic therapy was not significantly higher than the frequency of IFN negative patients requiring cytotoxic drugs (36/56 or 64% of IFN positive patients vs. 7/17 or 41% of IFN negative patients, p=0.09). Subsetting of the IFN positive patients in FIG. 6E revealed that the need for cytotoxic therapies was primarily associated with groups 0 and 2 (25/33 or 76% of groups 0 and 2 vs. 18/40 or 45% of all other patients, p=0.008).

To assess the degree of similarity between various gene expression signatures, signature scores were used to calculate correlation coefficients between each pair of signatures (Table 14). Summary statistics for the signatures used in FIGS. 5-6 are provided in Table 15.

TABLE 14

Correlations between gene signatures

|  | Ribosomal | Full mitochondrial | Condensed mitochondrial | Ribosomal/ mitochondrial | Neutrophil | IFN | Nuclear/ transcription |
|---|---|---|---|---|---|---|---|
| Ribosomal | 1.00 | 0.87 | 0.89 | 0.99 | 0.35 | −0.17 | −0.30 |
| Full mitochondrial | — | 1.00 | 0.98 | 0.93 | 0.43 | 0.11 | −0.51 |
| Condensed mitochondrial | — | — | 1.00 | 0.95 | 0.44 | 0.07 | −0.51 |
| Ribosomal/ mitochondrial | — | — | — | 1.00 | 0.38 | −0.10 | −0.37 |
| Neutrophil | — | — | — | — | 1.00 | 0.32 | −0.36 |
| IFN | — | — | — | — | — | 1.00 | −0.24 |
| Nuclear/ transcription | — | — | — | — | — | — | 1.00 |

Data are presented as r-values from the comparison of the indicated pairs of expression signature scores.

TABLE 15

Summary statistics for gene signatures

|  | Ribosomal/ mitochondrial | Neutrophil | IFN | Nuclear/ transcription |
|---|---|---|---|---|
| SLE | 8.4 ± 4.4 | 4.6 ± 2.0 | 26.9 ± 12.0 | 8.8 ± 3.1 |
| Control | 4.2 ± 1.3 | 2.2 ± 0.5 | 12.8 ± 2.7 | 14.5 ± 2.6 |
| p-value | 1.4 × 10$^{-12}$ | 3.2 × 10$^{-17}$ | 1.1 × 10$^{-16}$ | 7.7 × 10$^{-18}$ |

Data summarizing the indicated signature scores are presented as mean ± standard deviation, with p-value obtained from an unpaired t-test (SLE patients vs. controls).

Example 3

Identifying Genes That Can Be Used to Monitor and Predict SLE Activity

Collection of specimens for a human lupus biorepository was initiated. This study was designed to identify biomarkers for SLE. A lupus biorepository contains samples collected from the Hopkins Lupus Cohort Study (Petri et al., *Arthritis*

*Rheum* 34:937-44 (1991)), in which over 1,000 SLE patients are being followed, with clinic visits scheduled every three months. This study was designed to follow 300 patients for one year, including collection of clinical data and blood and urine samples at each visit during the enrollment year. The repository currently contains samples from over 1,350 individual patient visits of 297 enrolled SLE patients.

Study participants, clinical data, and biological specimens: Informed consent was obtained from each participant. A comprehensive medical history taken during the first visit of the study included a baseline SLICC/ACR damage index, which scores irreversible organ damage attributed to SLE (Gladman et al., *Arthritis Rheum* 39:363-9 (1996)). Detailed clinical data collected and recorded during each visit included several measures of disease activity: the SLE Disease Activity Index (SLEDAI; Bombardier et al., *Arthritis Rheum* 35:630-40 (1992)) which is weighted by organ system; the Systemic Lupus Activity Measure (SLAM; Liang et al., *Arthritis Rheum* 32:1107-18 (1989)) which grades symptoms and laboratory manifestations by severity; the British Isles Lupus Assessment Group measure (BILAG; Hay et al., *Q J Med* 86:447-58 (1993)) which reflects the physician's intention to treat based on organ-specific involvement; and a physician's global assessment (PGA) which is recorded on a 3 cm visual analog scale and represents the expert's judgment of clinical disease activity. Clinical data also included a medication history and a battery of clinical laboratory tests. Biological samples collected at each visit included RNA (extracted from whole blood using the PAXgene system from Qiagen/Becton-Dickinson), DNA, serum, plasma, peripheral blood mononuclear cells (cryopreserved), and urine. Clinical data collected prior to the beginning of the study were available in most cases, and data collection continued after the last study visit. For many of these patients, prospective clinical data extending over two and a half years were available.

Figure 7:
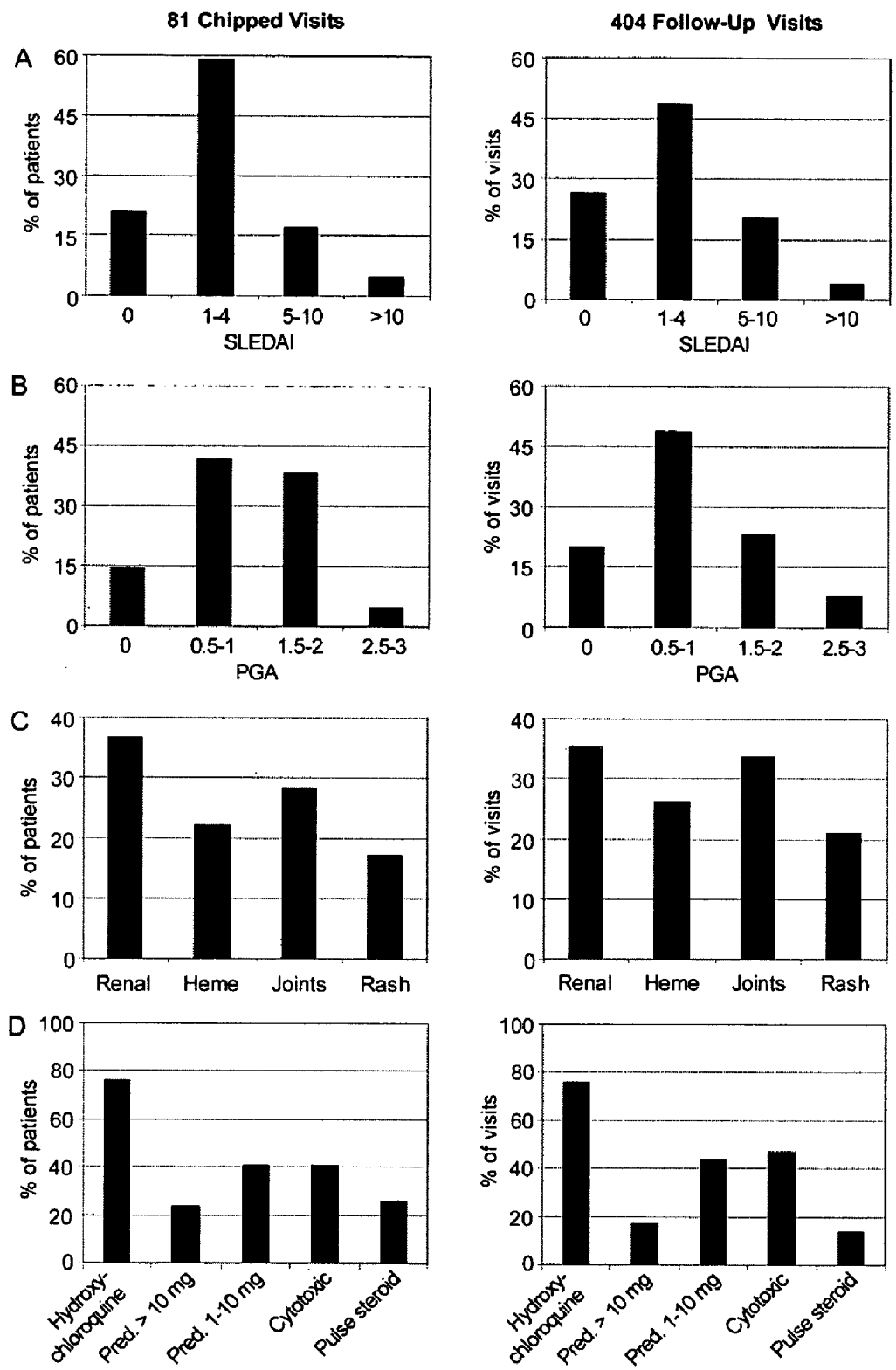
FIG. 7 is a series of graphs showing the spectrum of clinical features in the SLE cohort. Clinical data for the initial visits of 81 patients analyzed by microarray (left panels) and their 404 follow-up visits (right panels) are summarized. Shown are disease activity as measured by SLEDAI (A) and PGA (B), the frequency of selected clinical features (C), and use of specific medications (D).

Clinical features of SLE patients: The clinical spectrum of disease at baseline for the first 81 patients enrolled in the SLE study is summarized in FIG. 7, left panels. The patients demonstrated a range of clinical disease activity as measured by the SLEDAI (FIG. 7A, left panel) and by PGA (FIG. 7B, left panel). Renal involvement was observed in 37% of the patients, arthritis occurred in 28% of the patients, hematologic involvement occurred in 22% of the patients, and 17% of the patients had a rash (FIG. 7C, left panel). Most patients (77%) were taking the anti-malarial drug hydroxychloroquine, 64% were treated with steroids, and 41% were taking various immunosuppressive drugs (FIG. 7D, left panel). The patients were followed prospectively for 1.5 to 2.5 years, and cumulative statistics for the subsequent study visits were comparable with the baseline visit data (FIG. 7, right panels).

Processing of samples and microarrays: Blood from each of 81 SLE patients and 41 healthy controls was drawn into four PaxGene tubes (PreAnalytix, Franklin Lakes, N.J.). Total RNA was isolated according to the manufacturer's protocol, and on-column DNase treatment was performed. RNA yield and integrity were assessed using an Agilent Lab-on-a-Chip Bioanalyzer (Agilent Technologies, Inc., Palo Alto, Calif.). cRNA probes were generated and hybridized to Affymetrix U133A GeneChips according to standard Affymetrix protocols (Expression Analysis Technical Manual, Affymetrix, Santa Clara, Calif.). Seven of the 81 cRNA samples, generated using RNA from SLE patients, required two rounds of amplification. Following hybridization, the microarrays were washed, stained, and scanned. Affymetrix Microarray Suite 5.0 software was used to generate expression (or "signal") values for each gene after normalizing the microarrays by scaling the overall intensity of each microarray to 1500.

Gene markers for SLE activity: Microarray data were analyzed to identify genes associated with SLE disease activity. The correlation coefficient between each gene on the chip and the baseline visit SLEDAI was calculated. Using relatively stringent criteria ($r>0.3$, $p<0.01$), an initial group of 156 genes associated with disease activity was identified. Raw data for these 156 genes are presented in Table 16. Hierarchical clustering of the data was performed using Cluster and TreeView software (Eisen et al., *Proc Natl Acad Sci USA* 95:14863-8 (1998)). Prior to clustering, each expression value was divided by the mean signal of the 41 control subjects, and the $\log_2$ of this ratio was used as input data for the Cluster software. Hierarchical clustering of the data revealed two prominent clusters, an IFN signature and a distinct immunoglobulin (Ig) signature. The genes comprising these two clusters were among those that correlated most strongly with current SLEDAI.

TABLE 16

156 genes whose expression correlated with current SLEDAI ($r > 0.3$, $p < 0.01$)

| Accession No. | Gene |
| --- | --- |
| NM_006529 | glycine receptor, alpha 3 |
| NM_002477 | myosin, light polypeptide 5, regulatory |
| NM_006399 | basic leucine zipper transcription factor, ATF-like |
| NM_006701 | thioredoxin-like 4A |
| NM_003315 | DnaJ (Hsp40) homolog, subfamily C, member 7 |
| BC003186 | DNA replication complex GINS protein PSF2 |
| NM_000125 | estrogen receptor 1 |
| U37025 | sulfotransferase family, cytosolic, 1A, phenol-preferring, member 1 |
| U28169 | sulfotransferase family, cytosolic, 1A, phenol-preferring, member 2 |
| AI984980 | chemokine (C-C motif) ligand 8 |
| S69738 | chemokine (C-C motif) ligand 2 |
| NM_013276 | carbohydrate kinase-like |
| BE407516 | cyclin B1 |
| AF109196 | chloride intracellular channel 4 |
| NM_004349 | core-binding factor, runt domain, alpha subunit 2; translocated to, 1; cyclin D-related |
| BC000795 | signal-transducing adaptor protein-2 |
| AA931929 | AA931929 |
| NM_005609 | phosphorylase, glycogen; muscle (McArdle syndrome, glycogen storage disease type V) |
| AK025862 | AK025862 |
| NM_017723 | hypothetical protein FLJ20245 |
| AF010446 | major histocompatibility complex, class I-related |
| NM_003104 | sorbitol dehydrogenase |
| NM_006394 | regulated in glioma |
| BC005220 | chaperonin containing TCP1, subunit 8 (theta) |
| BF674842 | thymine-DNA glycosylase |
| NM_018444 | protein phosphatase 2C, magnesium-dependent, catalytic subunit |
| D26121 | splicing factor 1 |
| NM_002757 | mitogen-activated protein kinase kinase 5 |
| AL049748 | RNA binding motif protein 9 |
| AF241788 | nuclear distribution gene C homolog (*A. nidulans*) |
| NM_000900 | matrix Gla protein |
| AF216650 | methylthioadenosine phosphorylase |
| NM_001374 | deoxyribonuclease I-like 2 |
| NM_021057 | interferon, alpha 7 |
| AF074264 | low density lipoprotein receptor-related protein 6 |
| AF339807 | Transcribed locus, moderately similar to NP_955751.1 potassium channel regulator [*Homo sapiens*] |
| AL117546 | Transcribed locus, weakly similar to NP_079012.2 gasdermin domain containing 1 [*Homo sapiens*] |
| NM_002933 | ribonuclease, RNase A family, 1 (pancreatic) |
| NM_014498 | golgi phosphoprotein 4 |
| NM_001271 | chromodomain helicase DNA binding protein 2 |
| NM_006683 | family with sequence similarity 12, member A |
| NM_000290 | phosphoglycerate mutase 2 (muscle) |

TABLE 16-continued

156 genes whose expression correlated with current SLEDAI (r > 0.3, p < 0.01)

| Accession No. | Gene |
|---|---|
| AI380850 | AI380850 |
| AA211481 | LIM domain binding 3 |
| AI553791 | microtubule-associated protein 4 |
| NM_001481 | growth arrest-specific 8 |
| AI017382 | ataxin 7-like 1 /// ataxin 7-like 1 |
| AK021474 | AK021474 |
| AW083357 | interleukin 1 receptor antagonist |
| AF283773 | WD repeat domain 23 |
| NM_002753 | mitogen-activated protein kinase 10 |
| AW024233 | glycine-N-acyltransferase |
| NM_024046 | hypothetical protein MGC8407 |
| NM_002418 | motilin |
| AI133721 | AI133721 |
| X05610 | collagen, type IV, alpha 2 |
| NM_017545 | hydroxyacid oxidase (glycolate oxidase) 1 |
| NM_004854 | carbohydrate sulfotransferase 10 |
| AL022068 | AL022068 |
| AB051447 | AB051447 |
| NM_012434 | solute carrier family 17 (anion/sugar transporter), member 5 |
| AV728958 | talin 2 |
| NM_005925 | meprin A, beta |
| NM_000761 | cytochrome P450, family 1, subfamily A, polypeptide 2 |
| NM_002759 | protein kinase, interferon-inducible double stranded RNA dependent |
| BC005354 | BC005354 |
| BC000606 | BC000606 |
| NM_018579 | mitochondrial solute carrier protein |
| AJ249377 | AJ249377 |
| AI252582 | AI252582 |
| BC000603 | BC000603 |
| AW303136 | AW303136 |
| AI557312 | AI557312 |
| AK022897 | reversion-inducing-cysteine-rich protein with kazal motifs |
| NM_000770 | NM_000770 |
| NM_000243 | Mediterranean fever |
| N35896 | PTPRF interacting protein, binding protein 1 (liprin beta 1) |
| X60502 | sialophorin (gpL115, leukosialin, CD43) |
| U39945 | adenylate kinase 2 |
| BC004467 | enthoprotin |
| NM_013324 | cytokine inducible SH2-containing protein |
| BC001362 | 2',3'-cyclic nucleotide 3' phosphodiesterase |
| AF040105 | chromosome 6 open reading frame 108 |
| M62898 | annexin A2 pseudogene 2 |
| BC005902 | biliverdin reductase A /// biliverdin reductase A |
| NM_003896 | sialyltransferase 9 (CMP-NeuAc:lactosylceramide alpha-2,3-sialyltransferase; GM3 synthase) |
| NM_001643 | apolipoprotein A-II |
| AK026273 | AK026273 |
| M27968 | fibroblast growth factor 2 (basic) |
| M12350 | M12350 |
| NM_014221 | mature T-cell proliferation 1 |
| BF002474 | BF002474 |
| AA521272 | AA521272 |
| NM_000429 | methionine adenosyltransferase I, alpha |
| AF043294 | BUB1 budding uninhibited by benzimidazoles 1 homolog (yeast) |
| X84340 | X84340 |
| AW405975 | Ig lambda light chain variable region |
| AF043586 | Immunoglobulin lambda constant 2 (Kern-Oz-marker) |
| X93006 | Immunoglobulin lambda light chain V region (Humla203) /// Anti-HIV-1 gp120 immunoglobulin E51 lambda light chain /// Immunoglobulin lambda constant 2 (Kern-Oz-marker) /// Immunoglobulin lambda variable group /// Hepatitis B surface antigen antibody variable domain |
| D87021 | Ig lambda-chain V-J-C region (HCV-65) |
| AF043583 | IgG to Puumala virus G2, light chain variable region |
| BG482805 | Anti-HIV-1 gp120 V3 loop antibody DO142-10 light chain variable region |
| L14457 | L14457 |
| AJ249377 | Immunoglobulin lambda joining 3 |
| M20812 | Similar to Ig kappa chain |
| X79782 | Hypothetical protein similar to KIAA0187 gene product |
| M87790 | Anti-HIV-1 gp120 immunoglobulin E51 lambda light chain |
| D84140 | D84140 |
| AW408194 | immunoglobulin kappa variable 1D-13 |
| AJ408433 | AJ408433 |
| BG540628 | BG540628 |
| U80139 | IgM rheumatoid factor RF-SB1, variable heavy chain |
| L34164 | immunoglobulin heavy constant gamma 1 (G1m marker) /// immunoglobulin heavy constant gamma 1 (G1m marker) |
| AA476303 | AA476303 |
| AF078844 | AF078844 |
| BF246115 | metallothionein 1F (functional) |
| NM_030641 | apolipoprotein L, 6 |
| NM_001295 | chemokine (C-C motif) receptor 1 |
| AW008051 | agrin |
| NM_006084 | interferon-stimulated transcription factor 3, gamma 48 kDa |
| NM_017523 | XIAP associated factor-1 |
| BC002666 | guanylate binding protein 1, interferon-inducible, 67 kDa /// guanylate binding protein 1, interferon-inducible, 67 kDa |
| NM_003113 | nuclear antigen Sp100 |
| BF217861 | metallothionein 1E (functional) |
| NM_002450 | metallothionein 1X |
| N53555 | Sialoadhesin |
| AA749101 | interferon induced transmembrane protein 1 (9-27) |
| AL121994 | AL121994 |
| BF338947 | interferon induced transmembrane protein 3 (1-8U) |
| AJ243797 | three prime repair exonuclease 1 |
| NM_005138 | SCO cytochrome oxidase deficient homolog 2 (yeast) |
| AL031602 | AL031602 |
| AF333388 | AF333388 |
| NM_005951 | metallothionein 1H |
| NM_017414 | ubiquitin specific protease 18 |
| NM_001549 | interferon-induced protein with tetratricopeptide repeats 3 |
| NM_002534 | 2',5'-oligoadenylate synthetase 1, 40/46 kDa |
| NM_016817 | 2'-5'-oligoadenylate synthetase 2, 69/71 kDa |
| NM_002462 | myxovirus (influenza virus) resistance 1, interferon-inducible protein p78 (mouse) /// myxovirus (influenza virus) resistance 1, interferon-inducible protein p78 (mouse) |
| NM_006820 | chromosome 1 open reading frame 29 |
| NM_005101 | interferon, alpha-inducible protein (clone IFI-15K) |
| NM_004030 | interferon regulatory factor 7 |
| NM_005953 | NM_005953 |
| NM_005950 | metallothionein 1G |
| NM_002463 | myxovirus (influenza virus) resistance 2 (mouse) |
| AI862559 | hypothetical protein FLJ11286 |
| NM_000062 | serine (or cysteine) proteinase inhibitor, clade G (C1 inhibitor), member 1, (angioedema, hereditary) |
| NM_001953 | endothelial cell growth factor 1 (platelet-derived) |
| BC006333 | tripartite motif-containing 14 /// tripartite motif-containing 14 |
| NM_001188 | BCL2-antagonist/killer 1 |
| NM_018541 | NM_018541 |
| NM_017853 | thioredoxin-like 4B |
| AA457021 | BCL2-associated athanogene 5 |
| AA669336 | coagulation factor C homolog, cochlin (*Limulus polyphemus*) |
| N92920 | N92920 |
| X65232 | zinc finger protein 79 (pT7) |

The IFN signature, which showed a tight clustering of 35 transcripts, was found in 60 of the 81 cases (74%). Nearly all of the genes in this signature were also identified in a comparison of the 81 patients with a group of 41 controls.

The Ig signature identified in the initial gene list consisted of 18 immunoglobulin loci transcripts. This signature was suspected to reflect the presence of plasma cells in blood (Ginsburg et al., *Clin Exp Immunol* 35:76-88 (1979); Harada et al., *Br J Haematol* 92:184-91 (1996); Dorner and Lipsky, *Lupus* 13:283-9 (2004)). Therefore, a larger set of transcripts associated with current SLEDAI (r>0.19, p<0.05, n=1219 genes) was used to identify additional members of the Ig signature. This analysis identified 37 transcripts, 32 of which encoded the constant and variable regions of the kappa and lambda light chains, as well as IgM, IgD, and IgG heavy chains (represented by multiple probesets). Transcripts for the plasma cell specific surface marker CD38 were found in the expanded cluster. Another gene in the cluster, the thioredoxin-related gene TXNDC5, is a downstream target of X-box binding protein 1 (XBP-1; Shaffer et al., *Immunity* 21:81-93 (2004)). XBP-1 is a transcriptional regulator required for plasma cell differentiation (Reimold et al., *Nature* 412:300-7 (2001)). XBP-1 mRNA levels were correlated with SLEDAI (r=0.26, p=0.02) and with the other Ig signature transcripts (r=0.55, p=1.0×10-5), however XBP-1 did not cluster tightly with the other Ig/plasma cell transcripts. The expression of BLIMP-1, which regulates expression of XBP-1 in B cells (Shaffer et al., *Immunity* 17:51-62 (2002)), was not significantly correlated with either current SLEDAI (r=0.06, p>0.1) or with the level of Ig transcripts (r=−0.01, p>0.1). Three additional genes in the expanded Ig/plasma cell cluster (LOC91316, LOC91353 and KIAA0746) are not yet well characterized. Raw data for the genes comprising the Ig signature are presented in Table 17.

TABLE 17

37 Ig signature transcripts

| Accession No. | Gene |
|---|---|
| AA522514 | KIAA0746 protein |
| Z00008 | Ig kappa variable 1D-8 |
| BG340548 | IgM VDJ-region |
| NM_001775 | CD38 antigen (p45) |
| AJ275469 | Ig heavy constant delta |
| BG540628 | HRV Fab N8-VL |
| D87021 | Ig lambda-chain V-J-C region (HCV-65) |
| D84140 | Ig lambda variable 3-21 |
| AA398569 | similar to Ig lambda-like polypeptide 1 |
| L14457 | Ig rearranged kappa-chain gene V-J-region |
| AW408194 | Ig kappa variable 1D-13 |
| BG482805 | Anti-HIV-1 gp120 V3 loop antibody DO142-10 |
| AF103530 | Ig kappa light chain variable region |
| M87789 | Ig heavy constant gamma 1 (G1m marker) |
| L14458 | Ig rearranged kappa-chain gene V-J-region |
| AL022324 | LOC91353 |
| BG485135 | Anti-rabies virus Ig rearranged kappa chain V-region |
| BC005332 | Ig kappa constant |
| M87790 | Anti-HIV-1 gp120 Ig E51 lambda light chain |
| X57812 | Ig lambda constant 2 (Kern-Oz-marker) |
| NM_030810 | thioredoxin domain containing 5 |
| M85256 | Cationic anti-DNA autoantibody |
| AF103529 | Ig kappa light chain variable region |
| D84143 | Ig (mAb59) light chain V region |
| AJ249377 | Ig lambda joining 3 |
| X51887 | Ig kappa variable 1/OR2-108 |
| X79782 | Hypothetical protein similar to KIAA0187 gene product |
| M20812 | similar to Ig kappa chain |
| AJ408433 | Ig kappa chain variable region |
| BG536224 | HRV Fab N8-VL |
| AF043583 | IgG to Puumala virus G2, light chain variable region |
| X93006 | IgG lambda light chain V-J-C region |
| L23516 | IgG heavy chain V region |
| U80139 | IgM rheumatoid factor RF-SB1, variable heavy chain |
| M24669 | Ig heavy constant mu |
| AF047245 | Ig lambda light chain VJ region |
| AJ239383 | IgM rheumatoid factor RF-TT9, variable heavy chain |

Strong Ig/plasma cell signatures were found in 33 of the 81 baseline visits (41%). In all cases, the Ig/plasma cell signature was associated with the IFN signature. An Ig/plasma cell signature 'score' was derived for each patient. The Ig/plasma cell score was based on the 37 immunoglobulin transcripts (CD38, TXNDC5, 32 Ig transcripts, and 3 other genes), the expression levels of which were highly correlated with current disease activity as measured by SLEDAI. The Ig/plasma cell signature score was calculated by first normalizing the expression values for each row (Table 17) so that the maximum value in any row was 1.0. The columns (Table 17) were then summed to obtain the score. Several additional methods for calculating gene expression signature scores were also explored, and all yielded highly similar results (data not shown; see Baechler et al., *Proc Natl Acad Sci USA* 100: 2610-5 (2003)). Individuals with high levels of the immunoglobulin transcripts (N=33) had an Ig/plasma cell score of 11.5±5.8 (mean±SD), compared to 4.7±1.3 in the remaining patients (N=48) (p=1.3×10$^{-7}$). For comparison, a group of 41 matched controls showed an average Ig score of 5.3±1.7 (p=7.2×10$^{-7}$ versus Ig-positive SLE patients; p=not significant versus Ig-negative SLE; p=6.4×10$^{-4}$ versus all SLE).

In addition to its correlation with current SLEDAI, the Ig/plasma cell score was also significantly correlated with disease activity as measured by PGA and other measurements associated with active lupus, including elevated erythrocyte sedimentation rate (ESR) and low WBC and hematocrit (Table 18). Active renal disease was also associated with the Ig/plasma cell signature. There were modest correlations between the Ig/plasma cell score and use of certain medications (current use of ACE inhibitors, and historical use of immunosuppressive drugs and hydroxychloroquine). Anti-dsDNA antibodies were strongly correlated with the signature, suggesting that some of the plasma cells identified may be producing these antibodies. There was a significant correlation between African American ethnicity and the Ig/plasma cell signature, perhaps reflecting the increased prevalence of severe lupus in African American patients (Alarcon et al., *Arthritis Rheum* 41:1173-80 (1998)).

TABLE 18

Clinical features correlated with the Ig signature

| Clinical feature | r-value with Ig score | p-value LR[A] | p-value RP[B] |
|---|---|---|---|
| SLEDAI | 0.36 | p = 9.6 × 10$^{-4}$ | p = 0.004 |
| PGA | 0.33 | p = 0.002 | p = 0.001 |
| ESR | 0.33 | p = 0.004 | p = 0.003 |
| WBC | −0.23 | p = 0.04 | p = 0.04 |
| Renal | 0.25 | p = 0.02 | p = 0.02 |
| Hematocrit | −0.35 | p = 0.001 | p = 3.7 × 10$^{-4}$ |
| ACE-inhibitor | −0.22 | p = 0.05 | p = 0.03 |
| Hx[C] cytotoxic drugs | 0.21 | p = 0.07 | p = 0.05 |
| Hx plaquenil | −0.22 | p = 0.04 | p = 0.003 |
| Hx low C3 | 0.22 | p = 0.05 | p = 0.01 |
| Anti-dsDNA Abs | 0.34 | p = 0.002 | p = 0.01 |
| Hx of anti-dsDNA Abs | 0.20 | p = 0.08 | p = 0.02 |
| Hx leukopenia | 0.28 | p = 0.01 | p = 0.003 |
| Hx anemia | 0.23 | p = 0.04 | p = 0.01 |
| Ethnicity (African American) | 0.38 | p = 4.1 × 10$^{-4}$ | p < 1 × 10$^{-5}$ |

[A]p-value determined by linear regression analysis
[B]p-value determined by random permutation
[C]Hx, history In a parallel discovery path, the patient group was divided based on the Systemic Lupus Activity Measure—Revised (SLAM-R) disease activity index (Liang et al., *Arthritis Rheum* 32:1107-18 (1989); Bae et al., *Lupus* 10:405-9 (2001)), or a combination of PGA and the SLEDAI. Gene expression patterns were compared between 25 patients with high SLAM-R scores (≧5) and 25 patients with low scores (≦2). The following criteria were used to identify differentially expressed genes: (i) p<0.05 by unpaired student's t-test, (ii) average fold change of at least 1.5 when comparing the mean of active patients to the mean of inactive patients, and (iii) absolute difference of at least 100 signal units when comparing the means of the two groups. Of the 521 genes that were differentially expressed between these two patient groups (data not shown), the gene list included 15 Ig/plasma cell transcripts and 56 IFN-inducible genes. Similarly, a comparison of gene expression between patients with active disease by another definition (PGA≧1.5 and SLEDAI≧3, n=22) and patients with inactive disease (PGA≦1 and SLEDAI≦2, n=21) identified 344 transcripts, which included both IFN-responsive (n=35) and Ig/plasma cell genes (n=18). Together, these data provide further evidence for an association between the IFN and Ig/plasma cell signatures and active SLE.

Gene expression signatures and the prediction of future disease activity: Genetic algorithm testing (Gibson, *Biosystems* 23:219-28; discussion 229 (1989)) was applied to the set of SLEDAI-associated genes. The list of 1219 SLEDAI-associated genes was used as input for the genetic algorithm software (Agillence Software, Inc., Savage, Minn.). Ten genes were identified that showed the strongest correlations with SLEDAI. Raw data for the genes comprising the GA-10 signature are presented in Table 19. This set of genes included a representative from both the IFN signature (interferon induced transmembrane protein 1) and the Ig/plasma cell signature (HRV Fab N8-VL, kappa light chain variable region). An expression score (GA-10 score) based on these 10 genes was calculated as described above for the Ig/plasma cell signature. As expected, the GA-10 score was strongly correlated with current visit SLEDAI (r=0.85, p<1×10$^{-5}$), exceeding the highest correlation between any single transcript and current SLEDAI (Igλ joining 3, r=0.48, p=0.0001).

TABLE 19

GA-10 signature genes

| Accession No. | Gene |
|---|---|
| BC005902 | biliverdin reductase A |
| NM_022162 | caspase recruitment domain family, member 15 |
| AA669336 | coagulation factor C homolog, cochlin |
| NM_013255 | muskelin 1, intracellular mediator containing kelch motifs |
| U34919 | ATP-binding cassette, sub-family G (WHITE), member 1 |
| BG540628 | HRV Fab N8-VL |
| BF002474 | CTD small phosphatase-li |
| AL512697 | Similar to C10orf94 protein |
| NM_001384 | DPH2-like 2 (*S. cerevisiae*) |
| AA749101 | interferon induced transmembrane protein 1 (9-27) |

Patients were then sorted based on initial visit GA-10 scores, and disease activity, as measured by SLEDAI and PGA in the initial and subsequent visits to the clinic, was examined. Visualization of future disease activity, as measured by SLEDAI or PGA, was performed using TreeView software (Eisen et al., *Proc Natl Acad Sci USA* 95:14863-8 (1998)). There was a strong positive correlation between the initial visit GA-10 score and the maximum future SLEDAI observed in follow-up visits (r=0.48, p=3.0×10$^{-5}$). The GA-10 score also showed predictive value for future disease activity as measured by PGA at future visits (r=0.27, p=0.009). To assess the significance of the correlation between initial visit signature scores and the maximum future activity score (SLEDAI or PGA), p-values were calculated both by linear regression and by random permutation analysis of the dataset. The concordance of p-values generated using the two methods was very high, and the p-values reported reflect those obtained by random permutation.

The SLEDAI measurement alone at the baseline visit showed predictive value for future maximum SLEDAI (r=0.39, p=6.9×10$^{-4}$), suggesting that active disease at any given visit is predictive of future disease activity. A subset of the patient group was examined that consisted only of those cases where the initial visit SLEDAI was low (SLEDAI≦3, n=38 patients). In these patients with quiescent baseline disease activity, a positive and significant correlation was also observed between baseline visit GA-10 score and maximum future disease activity as measured by SLEDAI (r=0.32, p=0.03) or PGA (r=0.28, p=0.05).

Genetic algorithm gene groups of less than 10 transcripts showed reduced predictive power in these analyses (Table 20). Furthermore, the GA-10 score exhibited a higher correlation with maximum future activity (SLEDAI and PGA) than either the IFN or Ig signature alone (unpublished data).

Measuring gene expression levels for key blood cell transcripts at a single baseline clinic visit can be informative for current visit lupus disease activity and can be used in predicting the future course of disease.

TABLE 20

Ten-gene score yields higher correlation with current and future activity compared with scores based on fewer genes

| # of genes | Current SLEDAI | | Current PGA | | Max future SLEDAI | | Max future PGA | |
|---|---|---|---|---|---|---|---|---|
| | r-value | p-value | r-value | p-value | r-value | p-value | r-value | p-value |
| 1 | 0.48 | 6.0 × 10$^{-5}$ | 0.27 | 0.006 | 0.25 | 0.02 | 0.25 | 0.01 |
| 2 | 0.63 | <1 × 10$^{-5}$ | 0.21 | 0.03 | 0.31 | 0.006 | 0.05 | 0.31 |
| 3 | 0.70 | <1 × 10$^{-5}$ | 0.26 | 0.01 | 0.33 | 0.004 | 0.11 | 0.17 |
| 4 | 0.75 | <1 × 10$^{-5}$ | 0.17 | 0.06 | 0.46 | 1.0 × 10$^{-4}$ | 0.24 | 0.02 |
| 5 | 0.79 | <1 × 10$^{-5}$ | 0.27 | 0.007 | 0.33 | 0.003 | 0.15 | 0.10 |
| 10 | 0.85 | <1 × 10$^{-5}$ | 0.30 | 0.003 | 0.48 | 3.0 × 10$^{-5}$ | 0.27 | 0.009 |

Example 4

Neutrophil Gene Expression Signature in Human SLE

The neutrophil signature correlates with the percentage and absolute number of neutrophils as determined by concurrent complete blood count (CBC). The mitochondrial signature is also correlated with the neutrophil signature ($r=0.42$, $p=0.0001$), indicating that it derives, in part, from neutrophils, which are producers of oxidents. The neutrophil signature appears to be associated with current visit and historical evidence for renal disease. To identify genes associated with renal lupus, gene expression profiles were compared between patients with a history of renal disease (n=43) and patients with no renal involvement (n=38). One hundred and thirty three genes were identified that met the following criteria for differential expression: (i) $p<0.05$, (ii) average fold change>1.5, and (iii) absolute difference>100 signal units. These genes are listed in Table 21.

One gene cluster was identified that included several neutrophil genes (e.g., alpha-defensins, azurocidin). Investigation of the expression of these genes in purified cells from control donors demonstrated that these genes, which were observed to be highly expressed in patients with renal lupus, are neutrophil-specific in their expression. These results demonstrate that the genes listed in Table 21 can be used to identify mammals having renal lupus.

TABLE 21

Additional neutrophil signature

| Accession No. | Gene |
| --- | --- |
| BC003629 | RNA, U2 small nuclear |
| AI221950 | leucine-rich repeat protein, neuronal 3 |
| NM_002145 | homeo box B2 |
| NM_001870 | carboxypeptidase A3 (mast cell) |
| AF063002 | four and a half LIM domains 1 |
| AC003682 | zinc finger protein 134 (clone pHZ-15) |
| NM_025081 | KIAA1305 protein |
| AJ003062 | spindle pole body protein |
| AU147182 | Ras responsive element binding protein 1 |
| NM_002238 | potassium voltage-gated channel, subfamily H, member 1 |
| NM_000174 | glycoprotein IX (platelet) |
| BC001090 | MICAL-like 1 |
| NM_001279 | cell death-inducing DFFA-like effector a |
| AF061194 | ectodermal dysplasia 1, anhidrotic |
| AK026820 | ST3 beta-galactoside alpha-2,3-sialyltransferase 1 |
| BC005956 | relaxin 1 (H1) |
| AF116771 | tumor protein 63 kDa with strong homology to p53 |
| NM_020484 | NM_020484 |
| BG426689 | Thyroid hormone receptor associated protein 2 |
| AF070541 | hypothetical protein LOC284244 |
| NM_022146 | neuropeptide FF 1; RFamide-related peptide receptor |
| AK022765 | alpha-methylacyl-CoA racemase |
| NM_024819 | hypothetical protein FLJ22955 |
| AL136545 | transient receptor potential cation channel, subfamily M, member 3 |
| NM_003159 | serine/threonine kinase 9 |
| NM_022842 | CUB domain containing protein 1 |
| NM_012098 | angiopoietin-like 2 |
| M88162 | oculocerebrorenal syndrome of Lowe |
| NM_004933 | cadherin 15, M-cadherin (myotubule) |
| AW165979 | Zinc finger protein 609 |
| X81637 | *H. sapiens* clathrin light chain b gene |
| NM_005142 | gastric intrinsic factor (vitamin B synthesis) |
| AK027173 | Ring finger protein 24 |
| NM_001878 | cellular retinoic acid binding protein 2 |
| NM_014344 | four jointed box 1 (*Drosophila*) |
| U54826 | MAD, mothers against decapentaplegic homolog 1 (*Drosophila*) |

TABLE 21-continued

Additional neutrophil signature

| Accession No. | Gene |
| --- | --- |
| NM_025012 | hypothetical protein FLJ13769 |
| NM_002472 | myosin, heavy polypeptide 8, skeletal muscle, perinatal |
| AF052145 | chromosome 2 open reading frame 10 |
| L77561 | DiGeorge syndrome gene D |
| AI538172 | Retinoblastoma binding protein 6 |
| BE875592 | vesicle docking protein p115 |
| BG421209 | DEAD/H (Asp-Glu-Ala-Asp/His) box polypeptide 24 |
| AU147620 | AU147620 |
| AI685892 | fasciculation and elongation protein zeta 2 (zygin II) |
| AV684285 | hypothetical protein FLJ20719 |
| L06147 | golgi autoantigen, golgin subfamily a, 2 |
| AA664291 | SON DNA binding protein |
| BF965566 | leucine rich repeat (in FLII) interacting protein 1 |
| AI679073 | IQ motif containing GTPase activating protein 1 |
| AA699583 | ARP2 actin-related protein 2 homolog (yeast) |
| AI809341 | protein tyrosine phosphatase, receptor type, C |
| AI472757 | NS1-associated protein 1 |
| AW117498 | forkhead box O1A (rhabdomyosarcoma) |
| NM_006260 | DnaJ (Hsp40) homolog, subfamily C, member 3 |
| U14383 | mucin 8, tracheobronchial |
| AL121890 | chromosome 20 open reading frame 30 |
| AF339787 | Glypican 5 |
| AK022663 | similar to Hypothetical zinc finger protein KIAA1956 |
| AF207990 | fer-1-like 3, myoferlin (*C. elegans*) |
| NM_000804 | folate receptor 3 (gamma) |
| R25849 | R25849 |
| NM_000756 | corticotropin releasing hormone |
| NM_030929 | Kazal-type serine peptidase inhibitor domain 1 |
| AL031230 | glycosylphosphatidylinositol specific phospholipase D1 |
| AB040897 | RAN binding protein 10 |
| NM_017593 | homolog of mouse BMP-2 inducible kinase |
| NM_003851 | cellular repressor of E1A-stimulated genes |
| NM_000240 | monoamine oxidase A |
| T51252 | transmembrane and coiled-coil domain family 2 |
| R60866 | transcription factor Dp-1 |
| AL132665 | BCL2/adenovirus E1B 19 kD interacting protein 3-like |
| NM_006121 | keratin 1 (epidermolytic hyperkeratosis) |
| NM_002094 | G1 to S phase transition 1 |
| AL046979 | Tensin 1 |
| X77737 | solute carrier family 4, anion exchanger, member 1 |
| AF117233 | makorin, ring finger protein, 1 |
| AA133341 | Chromosome 14 open reading frame 87 |
| NM_019094 | nudix (nucleoside diphosphate linked moiety X)-type motif 4 |
| NM_021083 | Kell blood group precursor (McLeod phenotype) |
| NM_000140 | ferrochelatase (protoporphyria) |
| NM_001738 | carbonic anhydrase I |
| NM_030758 | oxysterol binding protein 2 |
| AL031178 | F-box protein 9 |
| AL035301 | phosphatidylinositol glycan, class C |
| AL049381 | Pre-B-cell leukemia transcription factor 1 |
| AA583044 | bone morphogenetic protein 2 |
| NM_003696 | olfactory receptor, family 6, subfamily A, member 1 |
| NM_005193 | caudal type homeo box transcription factor 4 |
| X90763 | keratin, hair, acidic, 5 |
| NM_002317 | lysyl oxidase |
| AI884858 | Putative prostate cancer tumor suppressor |
| NM_019060 | NICE-1 protein |
| AF005081 | chromosome 1 open reading frame 68 |
| X06409 | v-raf-1 murine leukemia viral oncogene homolog 1 |
| NM_014154 | HSPC056 protein |
| AF338650 | PDZ domain containing 3 |
| AB000277 | discs, large (*Drosophila*) homolog-associated protein 1 |
| AK024328 | ATP-binding cassette, sub-family A (ABC1), member 1 |
| AI435747 | chromosome 21 open reading frame 2 |
| AI762174 | zinc finger protein 42 (myeloid-specific retinoic acid-responsive) |
| NM_002886 | RAP2B, member of RAS oncogene family |
| AV705938 | neuronal Shc adaptor homolog |
| D84109 | RNA-binding protein gene with multiple splicing |
| AL121873 | ubiquitin-conjugating enzyme E2 variant 1 |
| NM_006980 | transcription termination factor, mitochondrial |
| AF306765 | aspartate beta-hydroxylase |
| NM_020415 | found in inflammatory zone 3 |

TABLE 21-continued

Additional neutrophil signature

| Accession No. | Gene |
| --- | --- |
| L33930 | CD24 antigen (small cell lung carcinoma cluster 4 antigen) |
| NM_001925 | defensin, alpha 4, corticostatin |
| NM_004084 | defensin, alpha 1, myeloid-related sequence |
| NM_001700 | azurocidin 1 (cationic antimicrobial protein 37) |
| M18728 | carcinoembryonic antigen-related cell adhesion molecule 6 |
| L35848 | membrane-spanning 4-domains, subfamily A, member 3 |
| NM_000607 | orosomucoid 1 |
| NM_018324 | thioesterase domain containing 1 |
| NM_001721 | BMX non-receptor tyrosine kinase |
| NM_003855 | interleukin 18 receptor 1 |
| NM_022746 | MOCO sulphurase C-terminal domain containing 1 |
| NM_003596 | tyrosylprotein sulfotransferase 1 |
| NM_000045 | arginase, liver |
| NM_004633 | interleukin 1 receptor, type II |
| BF513244 | Dishevelled associated activator of morphogenesis 2 |
| BC000903 | high-mobility group (nonhistone chromosomal) protein 2 |
| AA910946 | adaptor-related protein complex 1, mu 2 subunit |
| NM_020995 | haptoglobin-related protein |
| AF233437 | myotubularin related protein 3 |
| AC005390 | glutathione peroxidase 4 (phospholipid hydroperoxidase) |
| AL524520 | G protein-coupled receptor 49 |
| BE748563 | Hypothetical protein BC015148 |
| NM_007017 | SRY (sex determining region Y)-box 30 |
| BC005896 | hyaluronoglucosaminidase 3 |
| NM_001262 | cyclin-dependent kinase inhibitor 2C (p18, inhibits CDK4) |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for assessing effectiveness of a treatment for systemic lupus erythematosus, said method comprising:
providing a biological sample from a mammal having systemic lupus erythematosus disease and having received a treatment for said systemic lupus erythematosus disease, and
measuring gene expression in said sample to determine whether or not said mammal contains cells having an IFN signature 1 to a level less than that observed prior to said treatment,
wherein said IFN signature 1 comprises an expression profile comprising at least 60 percent of the genes listed in Table 5, and wherein the presence of said cells indicates that said treatment is effective.

2. The method of claim 1, wherein said mammal is a human.

3. The method of claim 1, wherein said cells are peripheral blood mononuclear cells.

4. The method of claim 1, wherein said treatment comprises an anti-IFN treatment.

5. The method of claim 4, wherein said anti-IFN treatment comprises a humanized anti-IFN antibody.

6. The method of claim 1, wherein said treatment comprises hydroxychloroquinone.

7. The method of claim 1, wherein said treatment comprises steroids.

8. The method of claim 1, wherein said treatment comprises an immunosuppressive drug.

9. The method of claim 1, wherein said biological sample comprises blood.

10. The method of claim 1, wherein said biological sample comprises serum.

11. The method of claim 1, wherein said biological sample comprises plasma.

12. The method of claim 1, wherein said biological sample comprises peripheral blood mononuclear cells.

13. The method of claim 1, wherein said biological sample comprises urine.

14. The method of claim 1, wherein said biological sample comprises total white blood cells, lymph node cells, spleen cells, or tonsil cells.

* * * * *

UNITED STATES PATENT AND TRADEMARK OFFICE
CERTIFICATE OF CORRECTION

PATENT NO. : 7,571,055 B2
APPLICATION NO. : 11/251589
DATED : August 4, 2009
INVENTOR(S) : Timothy W. Behrens It is certified that error appears in the above-identified patent and that said Letters Patent is hereby corrected as shown below:

On the Title Page, Item (73) Assignees, Regents of the University of Minnesota, please delete "Sint" and insert --Saint-- therefor;

On the Title Page, Item (56) References Cited, Foreign Patent Documents, WO 03/090694, please delete "11/2000" and insert --11/2003-- therefor;

On the Title Page, Item (56) References Cited, Other Publications, Asmal et al., please delete "CD4$^+$TCells" and insert --CD4$^+$ T Cells-- therefor;

Column 20, lines 12-13, please delete "hydroxychloroquinone" and insert --hydroxychloroquine-- therefor;

Column 50, line 22 (Claim 6), please delete "hydroxychloroquinone" and insert --hydroxychloroquine-- therefor.

Signed and Sealed this

Thirteenth Day of October, 2009

David J. Kappos
*Director of the United States Patent and Trademark Office*

UNITED STATES PATENT AND TRADEMARK OFFICE
CERTIFICATE OF CORRECTION

PATENT NO. : 7,571,055 B2 Page 1 of 1
APPLICATION NO. : 11/251589
DATED : August 4, 2009
INVENTOR(S) : Behrens et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 109 days.

Signed and Sealed this

Seventh Day of September, 2010

David J. Kappos
*Director of the United States Patent and Trademark Office*